United States Patent [19]

Bennett

[11] Patent Number: 4,930,997

[45] Date of Patent: Jun. 5, 1990

[54] PORTABLE MEDICAL SUCTION DEVICE

[76] Inventor: Alan N. Bennett, 2342 Hosp Way, Carlsbad, Calif. 92008

[21] Appl. No.: 87,153

[22] Filed: Aug. 19, 1987

[51] Int. Cl.$^5$ .................. F04B 39/14; A61M 31/00
[52] U.S. Cl. .................. 417/410; 604/319; 418/178
[58] Field of Search ............ 604/250, 251, 319, 317; 418/152, 178; 417/410

[56] References Cited

U.S. PATENT DOCUMENTS

| | | | |
|---|---|---|---|
| 2,558,837 | 7/1951 | Frei | 418/69 |
| 2,616,615 | 11/1952 | Scott | 418/152 |
| 2,989,769 | 6/1961 | Houser . | |
| 3,267,510 | 8/1966 | Cote . | |
| 3,468,260 | 9/1969 | Belden | 418/152 |
| 3,515,135 | 6/1970 | Flower et al. . | |
| 3,552,895 | 1/1971 | Bayley | 418/178 |
| 3,599,639 | 8/1971 | Spotz . | |
| 3,610,781 | 10/1971 | Kolb | 417/368 |
| 3,648,698 | 3/1972 | Doherty | 604/319 |
| 3,665,919 | 5/1972 | Laerdal . | |
| 3,783,867 | 1/1974 | Summersby | 604/151 |
| 3,885,567 | 5/1975 | Ross | 604/151 |
| 4,123,201 | 10/1978 | Andriules | 417/410 |
| 4,251,192 | 2/1981 | Clark | 418/266 |
| 4,306,558 | 12/1981 | Kurtz et al. . | |
| 4,347,874 | 9/1982 | Sullivan | 604/250 |
| 4,376,620 | 3/1983 | Colston . | |
| 4,398,872 | 8/1983 | Fleenor | 417/360 |
| 4,403,611 | 9/1983 | Babbitt et al. . | |
| 4,435,171 | 3/1984 | Goldberg | 603/317 |
| 4,487,606 | 12/1984 | Levifon | 604/319 |
| 4,569,674 | 11/1986 | Phillips | 604/319 |
| 4,631,061 | 12/1986 | Martin . | |
| 4,675,010 | 6/1987 | Siposs | 604/319 |
| 4,795,448 | 3/1989 | Stacey | 604/319 |

FOREIGN PATENT DOCUMENTS

| | | | |
|---|---|---|---|
| 952391 | 8/1974 | Canada . | |
| 1615201 | 5/1978 | Fed. Rep. of Germany . | |
| 3441893 | 5/1986 | Fed. Rep. of Germany | 604/319 |
| 2582519 | 12/1986 | France | 604/319 |

OTHER PUBLICATIONS

Suction Devices A Guide to Emergency Field Aspirators by Thom Dick, Mar. 1985, 15 pages.
Health Devices A Test, Evaluation, and Advisory Service of the Emergency Care Research Institute, Mar. 1978, vo. 7, No. 5, 25 pages.
Standard Specification for Medical and Surgical Suction and Drainage Systems American Society for Testing and Materials, Designation F960-86, (10 pages).

Primary Examiner—Leonard E. Smith
Assistant Examiner—David W. Scheuermann
Attorney, Agent, or Firm—Woodard, Emhardt, Naughton, Moriarty & McNett

[57] ABSTRACT

The portable medical suction device of the preferred embodiment of the present invention comprises a disposable suction component including a suction tube bonded to the inlet of a plastic flow-through rotary vane pump, a collection tube bonded to the pump outlet and a flexible reservoir bag bonded to the collection tube and having a hydrophobic vent, adapted to be economically disposed of after a single use without the necessity of cleaning the components of the device that contact the aspirate. The rotary vane pump of the disposable component is designed for ready operable coupling and decoupling to the output of an electric motor. The motor is removably mounted in a support frame. The reservoir bag is also gathered within the support frame, having a first volume capacity when so gathered and a second larger volume capacity when unfolded through an opening at one end of the support frame. The motor is energized by a rechargeable battery through an electronic control assembly, each of which is removably mounted in the support frame. The electronic control assembly includes circuitry capable of generating three discrete suction levels for various types of suctioning environments. An AC/DC converter and an external DC power cable are removably housed within the support frame, usable to recharge the battery or drive the motor. The entire suction device is small, lightweight and encased in a padded carrying case having a plurality of readily openable and closeable openings for access to the various components of the suction devce.

24 Claims, 10 Drawing Sheets

PORTABLE MEDICAL SUCTION DEVICE

BACKGROUND OF THE INVENTION

The present invention relates to a suction device, in particular for emergency medical purposes, which can be used for the withdrawal by suction of aspirate or foreign substances in the oral or nasal cavity of a patient requiring resuscitation.

Frequently in medical emergencies, the patient ingests foreign substances that accumulate in the oral/nasal cavity. For instance, in drowning persons, water or sludge may enter the oral/nasal cavity, and it frequently happens that unconscious patients requiring resuscitation vomit and aspirate the vomitus. In cases of trauma to the head, bleeding into the oral/nasal cavities can occur, and blood and clots can block the airway. In these circumstances, it is of primary importance to keep the airway open and free of accumulations of foreign substances or vomitus. Airway management is particularly important in the emergency medical field, where the patient or victim is remote from a hospital and hospital equipment. In this environment, the suction devices must be portable and capable of withdrawing whatever aspirate or substance may have accumulated in the oral or nasal cavities of the patient.

Suction devices of the type under discussion will form an integral part of first aid equipment used by emergency medical personnel. These suction devices must be as small and as lightweight as possible since they are to be used under a variety of conditions and in a variety of locations. In order to be an effective emergency unit for field use, a suction device must comply with certain minimum standards, such as those established by the Emergency Care Research Institute, as reported in an article entitled "portable Suction Sources" in the March, 1978 issue of "Health Devices", Vol. 7, No. 5, as set forth in the March, 1985 issue of "Jems" in an article by Thom Dick entitled "Suction Devices: A Guide to Emergency Field Aspirators", and as defined in ASTM Designation F960-86 "Standard Specification for Medical and Surgical Suction and Drainage Systems" published in March, 1986. The above-mentioned articles in the periodicals "Health Devices" and "Jems", as well as the ASTM Designation, are incorporated by reference herein, including their discussions of the operation of medical suction devices.

In general terms, the "JEMS Suction Model" described in the above-identified March, 1985 issue of "Jems" illustrates the optimum suction device. According to the Jems standard, the device should provide a suction level for oropharyngeal suctioning of up to 500 mm Hg at full airflow with the collection bottle in place, although a typical value of 300 mm Hg is acceptable. The device should reach this maximum suction level within 3 seconds of initiation. The free flowrate should be at least 30 liters per minute (lpm). so that the patient can be fully suctioned in as short a time as possible to reduce the risk of asphyxiation and the corrosive effects of vomitus or even emesis collected in the airways. Since aspirate and foreign substances can accumulate in the lungs and in the nasal cavities, the portable suction device should be capable of providing a free flow rate of 25 lpm at a lower suction level of around 100–150 mm Hg, such as for endotracheal suctioning, to prevent damage to the delicate mucosa linings. The collection receptacle for the aspirate should be unbreakable and have adequate capacity to hold the aspirate, typically between 500 and 1,000 milliliters (ml.).

According to the Jems standard, the optimum suction device should be compact and lightweight, since the medical personnel may be required to transport the suction device directly to an accident site where access is limited and difficult. The suction apparatus must be reliable and capable of providing a sustained suction for at least 60 minutes without being fouled by the aspirate or foreign substance being suctioned. The unit should also be capable of short-term intermittent use necessary to reduce the risk of hypoxia as the suction device removes more air than the patient can breathe. An optimum apparatus should have easily and quickly replaceable components, in particular the collection receptacle in the event the receptacle is overflowed. The device should further be protected from damage to its hardware, particularly metal components, should an overflow occur.

Portable suction devices come in a variety of designs, including manual pumps, gas powered devices, and battery powered electric devices. The vacuum source or pump, is also available in a variety of types, such as diaphragm, double-action piston, peristaltic, and rotary vane devices. Representative devices are described in the "Health Devices" and "Jems" publications incorporated by reference into this specification.

To applicant's knowledge, none of these prior art devices combines a modular design that is compact and lightweight with a suction system that is virtually leak-proof and that is economical to dispose of after each use. The vast majority of the prior art devices have a very limited range of orientations in which the suction device can be operated without leakage into the electrical and mechanical components of the apparatus. Furthermore, these devices carry with them the risk of cross-contamination of the medical technician who must remove and clean the collection receptacle and suction equipment after each use. This can be a particular concern where the patient is carrying a highly communicable and contagious disease, under which circumstances it is preferable to reduce the risk of contact with the suctioned aspirate or foreign substance. Moreover, none of these suction devices satisfy the optimum criteria established for the "JEMS Suction Model" generally described above.

SUMMARY OF THE INVENTION

A portable suction device comprises rotation means for providing rotary motion and disposable and readily removeable collection means for removing and collecting a suspension when the rotation means is providing rotary motion. The collection means includes a suction tube, a collection container and a pump, having a working member operating on the suspension being pumped and a rigid housing in which the working member operates. The pump is connected at its inlet to the suction tube and at its outlet to the collection container. The pump includes coupling means for allowing readily operable coupling and decoupling to the output of the rotation means.

DESCRIpTION OF THE pREFERRED EMBODIMENTS

Figure 1:
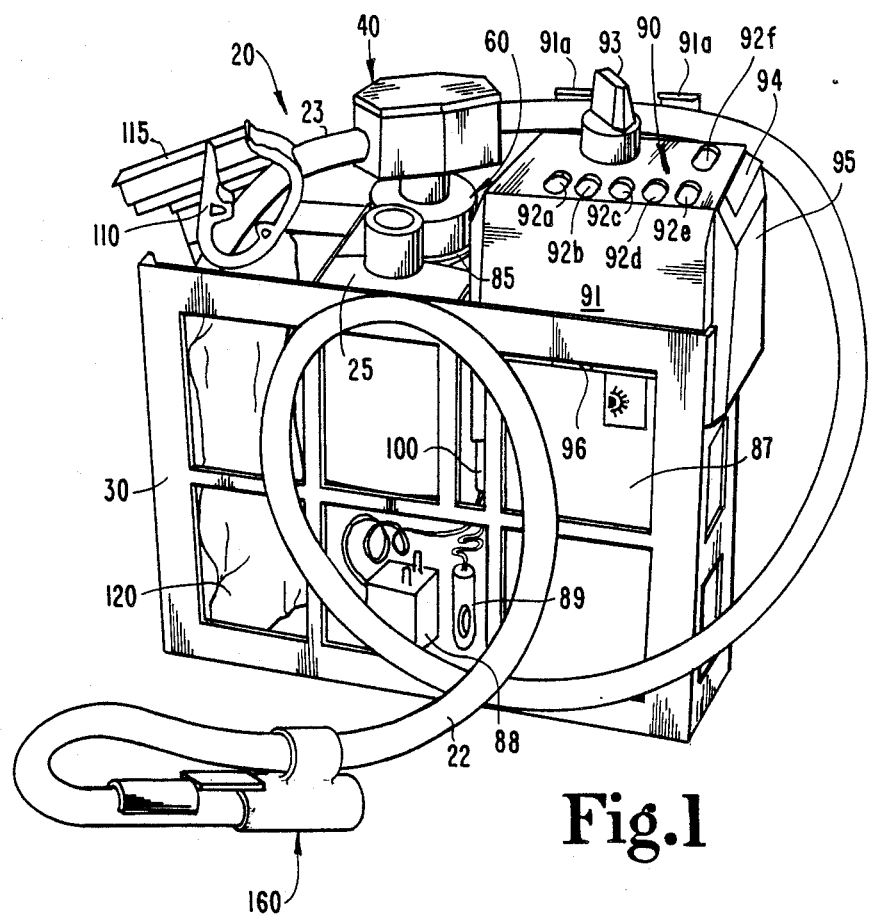
FIG. 1 is a perspective view of the portable medical suction device of the preferred embodiment, shown with the components of the device mounted in a support frame.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The portable medical suction device 20 of the preferred embodiment, illustrated in FIG. 1, comprises a support frame 30, shaped in a parallelopiped configuration, with a variety of openings designed to house the various components of the suction device. Mounted in support frame 30 are motor 85 with drive interface assembly 60 integrating the motor with pump assembly 40, battery 87 providing power to motor 85, and electronic control assembly 90 between battery 87 and motor 85 for controlling the motor rotational speed, monitoring the battery charge and recharging the battery 87. Also mounted in support frame 30 are AC/DC converter 88 for recharging battery 87, external DC power cable 89 for interfacing with an alternate power source for motor 85 or to recharge battery 87, reservoir bag 120 connected to the outlet of pump assembly 40 by collection tube 23, and rinse bottle 25 for rinsing a catheter to be used with portable medical suction device 20.

Suction tube 22, attached at the inlet of pump assembly 40, is used to suction aspirate or foreign substances from the patient. Reservoir bag 120 includes a hydrophobic filter 115 that allows passage of air therethrough while remaining liquid leakproof. Tube clamp 110 is engaged on collection tube 23 to provide a means to clamp the collection tube after suctioning has been completed.

Figure 2:
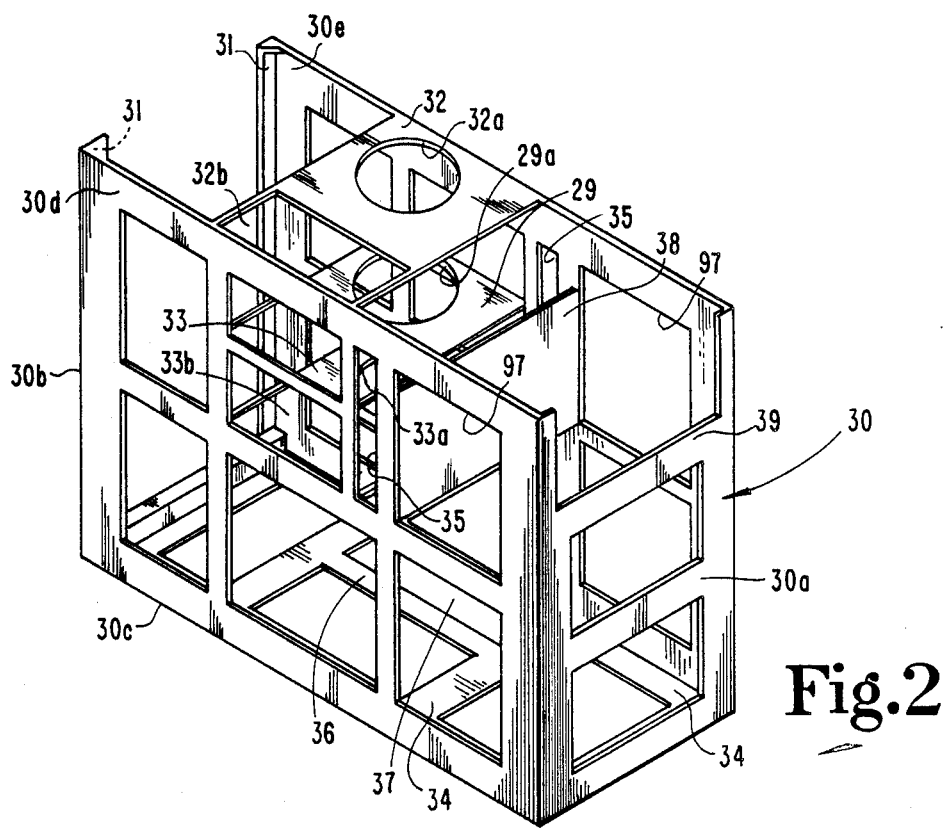
FIG. 2 is a perspective view of the support frame from FIG. 1, shown with no components mounted therein.

Portable medical suction device 20 is of a modular construction so that all of the components comprising the suction device can be removed from support frame 30 independent of other components. Support frame 30 has been specifically designed in the present embodiment to enhance the modular construction of suction device 20. Referring to FIG. 2, support frame 30 is shown as having a first end wall 30a, second end wall 30b, bottom wall 30c, first side wall 30d, and second side wall 30e. The top of support frame 30 is generally open. Each of the walls 30a-30e include several openings therethrough to allow free access to the components of suction device 20 and to reduce the amount of material required to fabricate support frame 30. Support frame 30 is generally hollow within walls 30a-30e. The manufacturing costs for this support frame can be reduced, at the expense of weight and material requirements, if walls 30a-30e are made without the several openings, except where required for access to components.

At end wall 30b, there are a pair of collection bag retaining walls 31 second end wall 30b being open with the exception of retaining walls 31. Thus, reservoir bag 120 can fit in the interior of support frame 30 and can be easily accessed through the open portion of second end wall 30b and the open top of support frame 30. Collection bag retaining walls 31 provide some restraint for reservoir bag 120 to keep it within the interior of support frame 30. The configuration of second end wall 30b also allows reservoir bag 120 to be expanded between retaining walls 31 to increase the volume capacity of reservoir bag 120 during use, as will be described in more detail herein.

At approximately mid-length along support frame 30, there is a pump assembly support platform 32 spanning the top of support frame 30 between first and second sidewalls 30d and 30e. Support platform 32 includes a support opening 32a and a first access opening 32b therethrough. Directly beneath support platform 32 there is an intermediate support platform 29 and a motor support platform 33, each having openings therethrough aligned with the openings in support platform 32. Thus, intermediate support platform 29 includes an access opening 29a, and motor support platform 33 includes motor support opening 33a, each of these openings lying directly beneath support opening 32a. Similarly, intermediate support platform 29 includes second access opening 29b and motor support platform 33 includes third access opening 33b aligned with first access opening 32b. Each of the access openings 32b, 29b and 33b provide support for rinse bottle 25 inserted therein. Motor 85 is inserted through openings 32a, 29a and 33a. Motor support opening 33a has a smaller diameter than openings 32a and 29a so that motor support platform 33 can provide a support surface on which motor 85 can rest. Openings 32a and 29a have a diameter slightly smaller than the diameter of motor 85 so that the motor can be easily pressed into or removed from support frame 30, while preventing longitudinal and rotational motion of the motor body within the frame.

Adjacent the motor support platforms is a portion of the interior of support frame 30 forming a channel for housing electronic cables and connectors, defined generally by connector channel openings 35 in first and second sidewalls 30d and 30e. A connector 100 from electronic control assembly 90 to motor 85, AC/DC converter 88 and external DC power cable 89 resides within the connector channel. Beneath the motor support platforms and the connector channel is a space in the interior of support frame 30 for the AC/DC converter 88. Bottom wall 30c includes an AC/DC converter support floor 36 on which the converter 88 rests. AC/DC converter access opening 37 is formed in bottom wall 30c and second sidewall 30e to provide access to the converter. Access opening 37 also provides access to the connector residing within the connector channel portion of the interior of support frame 30.

Electrical housing enclosure wall 38 spans the interior of support frame 30 between first and second sidewalls 30d and 30e. Enclosure wall 38 also further defines the connector channel portion of the support frame interior. Enclosure wall 38, along with electrical housing support wall 39 in first end wall 30a provides a support surface on which housing 91 of electronic control assembly 90 rests. Openings in first and second sidewalls 30d and 30e include a latch interface edge 97 that is engaged by latch 96 on electronic control assembly housing 91 to hold the housing in position against enclosure wall 38 and support wall 39. Thus, electronic control assembly 90 is locked in place in the modular support frame 30, and can be released by depressing latches 96 on opposite sides of housing 91, or by expanding first and second sidewalls 30d and 30e at their latch interface edges 97. Battery 87 resides in the interior of support frame 30 directly beneath electronic control assembly 90 and is also locked in position by latches 96 on housing 91. Bottom wall 30c includes a battery support floor 34 on which battery 87 rests.

It is apparent from the description of support frame 30 that the support frame allows for modular assembly and disassembly of portable medical suction device 20. Specific portions of the interior of support frame 30 are provided for each of the elements of the suction device. Furthermore, it is possible to access specific components without disturbing the remaining components of suction device 20.

Referring again to FIG. 1, the central element of portable medical suction device 20 is the disposable component comprising suction tube 22, pump assembly 40, collection tube 23, reservoir bag 120, and hydrophobic filter 115. In prior art suction devices, it is typically necessary to wash and disinfect the suction components of the apparatus, particularly the collection chamber, after use. The "JEMS Suction Model" referenced above specifies one criterion that the collection chamber be designed to be sanitized, rinsed and dried within one minute. Although most of the prior art devices incorporate some means to prevent overflow into the pump components of the suction device, if an overflow should occur it is also necessary to wash and disinfect the pump elements. If these devices are not immediately disassembled, cleaned and relubricated, permanent damage may occur. Overflow into the pump of these prior art devices can disable the entire suction system. Moreover, if the patient is carrying a contagious or communicable disease, there exists a risk of cross-contamination of medical personnel who must clean the suction components of the medical suction apparatus. In the present invention, the suction elements that come in contact with the aspirate or foreign substance extracted from the patient are manufactured of inexpensive material and arranged to be easily removed and discarded once the suction device 20 has been used.

In the preferred embodiment, suction tube 22, collection tube 23 and reservoir bag 120 are composed of F.D.A. approved vinyl, While pump assembly 40 is formed of clear acrylic. Only collection tube 23 and reservoir bag 120 are composed of medical grade vinyl to avoid contamination of resuscitated aspirate by plasticizers found in some grades of vinyl. Each of these materials, vinyl and acrylic, are inexpensive to obtain and to manufacture. Furthermore, the suction elements are designed for a usable life equal to the maximum expected duration of suctioning for a single patient, typically about two hours. Thus, the present invention presents an economical alternative to washing and reusing the suction components of the portable medical suction device. Once suction device 20 has been used, and reservoir bag 120 is filled with aspirate, all the suction elements can be removed from modular support housing 30 and disposed of by medical personnel, without risk of cross-contamination from the contents of reservoir bag 120. As described above, reservoir bag 120 is easily removable from its portion of the interior of support frame 30. Pump assembly 40 is also easily removable via a "twist-lock" feature of drive interface assembly 60, described in detail herein. Suction tube 22 is normally held in position by tube retainers 91a integral with electronic control assembly housing 91. When suction device 20 has been used, suction tube 22 may be easily disengaged from tube retainers 91a. A tube retainer 160 (FIG. 16, infra) is provided to seal the suction end of tube 22 to prevent any leakage of aspirate from the open end. Once removed from support frame 30, all of the above components can be disposed of without risk of cross-contamination.

As an additional safeguard, rinse bottle 25 is provided to normally carry a supply of water. Once suctioning of the patient has been completed, the medical personnel can insert suction tube 22, with or without a catheter attached at its end, into rinse bottle 25 to pump water through suction tube 22, pump assembly 40 and collection tube 23 into reservoir bag 120. Water flowing through the suction elements will satisfactorily clean out aspirate accumulated in these elements after suctioning is complete to further minimize the risk of cross contamination.

Figure 3:
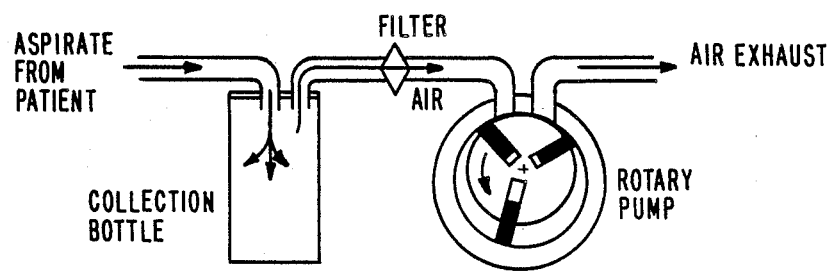
FIG. 3 is a schematic showing the flow path of suction devices of the prior art.

In order to produce a portable medical suction device having completely disposable suction elements, it is necessary to divert from the normal philosophies of prior art suction devices and to develop or apply a new technology to the field of portable medical suction devices. In the great majority of prior art devices, the collection bottle for collecting aspirate from the patient is interposed between the suction tubing to the patient and the suction pump. As shown in FIG. 3 a prior art rotary pump suction device has an inlet tubing into the collection bottle taking aspirate from the patient and depositing it in the collection bottle. A vacuum is produced by the rotary pump and air is continually suctioned from the collection bottle, creating a vacuum in the collection bottle which in turn suctions the aspirate from the patient. Thus one disadvantage in these prior art devices is that air residing in the collection bottle must be suctioned by the pump before a vacuum is created at the patient end of the suction tubing. A filter is interposed in the air line from the collection bottle to the rotary pump to avoid the possibility of any aspirate or airborne bacteria flowing into and contaminating the rotary pump. In prior art devices of this sort, it is absolutely essential that no aspirate enter the air line between the collection bottle and the rotary pump, because the aspirate will contaminate and frequently foul up or jam the rotary pump. In other suction devices of the prior art, the rotary pump is replaced by a peristaltic pump, a bellows, a venturi, or a double-action piston pump, such as those described in the publication "Health Devices" incorporated above by reference. In the devices of the prior art, significant portions of the suction producing elements are composed of metal leading to the risk of corrosion, as well as rendering the suction element expensive to replace if made disposable. In the peristaltic devices, contamination of the rotating components is not a concern because the aspirate flows through a tube that contacts the rotating components. However, a peristaltic pump requires a tube having sufficient elasticity to be deformed by the rollers, sufficient rigidity to hold its shape during use, and adequate strength to withstand continuous deformation, without adhesion and/or collapse.

Figure 4:
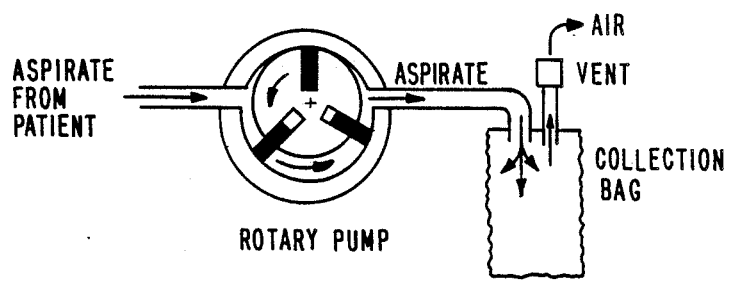
FIG. 4 is a schematic showing the flow path of the suction device of the preferred embodiment.
Figure 5:
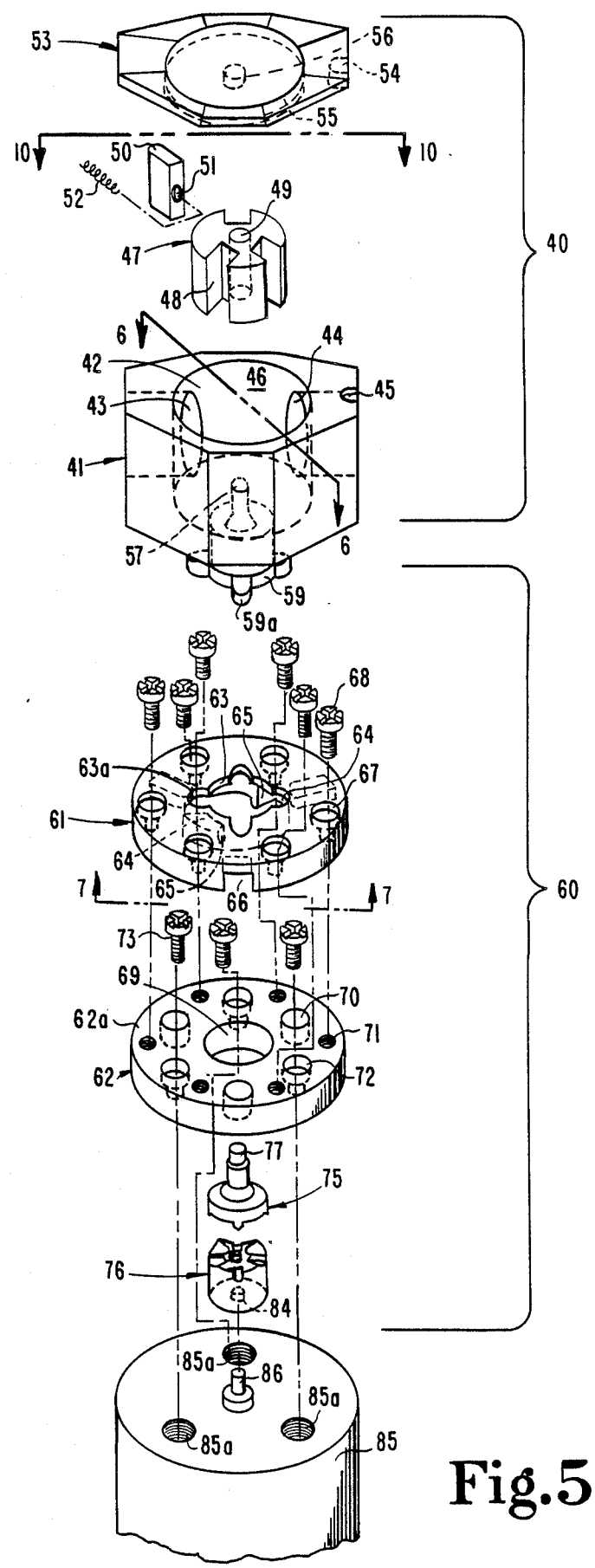
FIG. 5 is an exploded perspective view of the pump assembly and the drive interface assembly of the present invention.

In the portable medical suction device 20 of the present invention, disposability of the suction elements is made possible by interposing the suction producing elements between the patient and the collection bag, as illustrated in FIG. 4. In the present invention, aspirate from the patient enters the rotary pump and is transmitted through the pump to an outlet tube that communicates with the collection bag. An air vent in the collection bag allows air in the bag and mixed with the aspirate to vent to the atmosphere while solid particles and liquids accumulate in the collection bag. In this respect, the suction producing element of the present invention can be described generally as a "flow-through" pump, since the aspirate from the patient flows through the pump unlike the prior art devices (except for those with peristaltic pump) in which the aspirate flows directly into the collection bottle.

The details of pump assembly 40 and drive interface assembly 60 will be described with reference to FIGS. 5-10. Drive interface assembly 60 integrates pump assembly 40 with the rotational output from motor 85. Since pump assembly 40 of the present invention is designed to be disposable, some means must be provided for disengaging the pump assembly from output shaft 86 of motor 85. Since portable medical suction device 20 is intended for field use, it is also necessary that removal of pump assembly 40 be effected easily and quickly, and that a replacement pump assembly be equally quickly and easily reinstalled. It is to address this problem that the "twist-lock" feature of suction device 20 of the present invention was created. Pump assembly 40 includes pump body 41 within which the pumping and suctioning action occurs. Pump body 41 includes a twist-lock flange 59 projecting from the bottom of pump body 41. Flange 59 includes several twist-lock tongues 59a, four in number in the present case, spaced at 90° intervals around flange 59. The "twist-lock" feature also includes twist-lock plate 61 having a twist-lock bore 63 extending centrally therethrough. The perimeter of twist-lock bore 63 is shaped generally identical to the plan view of twist-lock flange 59. Twist-lock bore 63 includes several tongue receiving slots 63a that are shaped and located to receive the several twist-lock tongues 59a integral with twist-lock flange 59.

Figure 6:
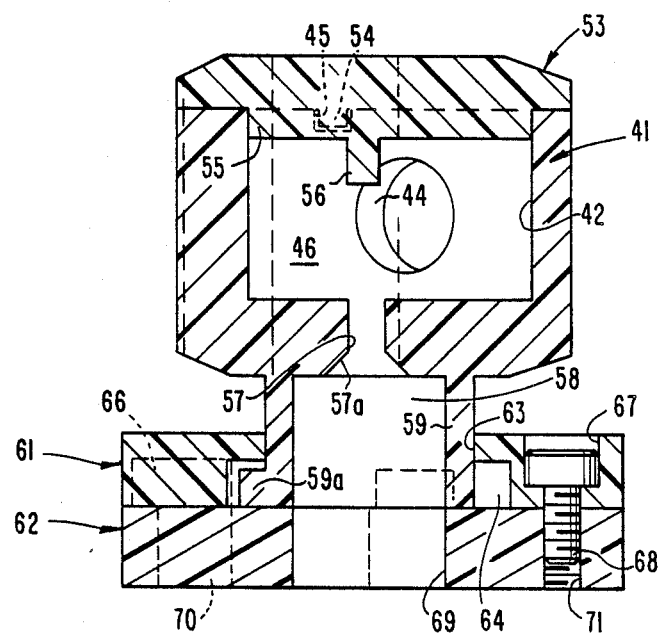
FIG. 6 is a cross-sectional view of the pump assembly and drive interface assembly taken along the line 6—6 in FIG. 5 and viewed in the direction of the arrows, shown without the rotating components of the two assemblies.
Figure 7:
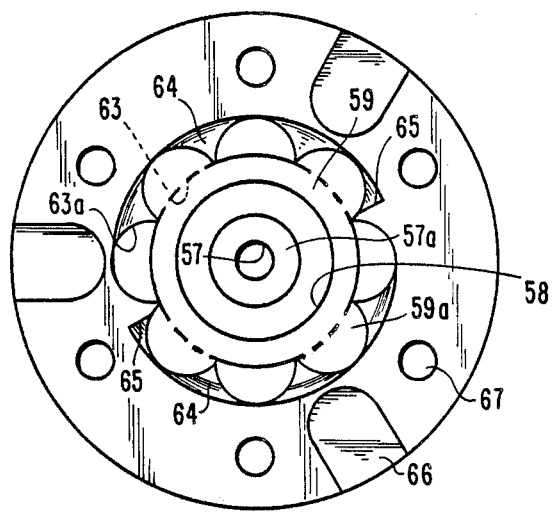
FIG. 7 is a bottom view of the twist-lock elements of the drive interface assembly of the present invention, as viewed in the direction of the arrows along the line 7—7 in FIG. 5.

Contiguous with twist-lock bore 63 are a pair of locking recesses 64, as best illustrated with reference to FIGS. 6 and 7 Each of the locking recesses 64 open at one end into a tongue receiving slot 63a, and continue circumferentially about 150 degrees, terminating in a stop wall 65 adjacent another tongue receiving slot 63a. Thus, as illustrated in FIG. 7, each locking recess 64 opens into two tongue receiving slots 63a, one slot at one end of locking recess 64 and another slot circumferentially midway along locking recess 64.

In the operation of this "twist-lock" feature, twist-lock flange 59 is inserted into twist-lock bore 63, with twist-lock tongues 59a initially aligned with tongue receiving slots 63a. Once twist-lock tongues 59a have entered locking recess 64, twist-lock flange 59 is rotated until at least one of the several twist-lock tongues 59a abuts a stop wall 65 terminating the locking recesses 64. As viewed in FIG. 7, twist-lock flange 59 is rotated clockwise once twist-lock tongues 59a have been inserted into locking recess 64. The interaction between twist-lock tongues 59a and locking recesses 64 keeps pump assembly 40 mounted on drive interface assembly 60 during operation. When portable medical suction device 20 is operated, rotational output from output shaft 86 of motor 85 is also clockwise as viewed in FIG. 7. Thus torque passing from output shaft 86 to twist-lock flange 59 will tend to keep twist-lock tongues 59a abutting stop walls 65. This "twist-lock" feature, therefore, prevents accidental disengagement of pump assembly 40 from drive interface assembly 60 during operation of portable medical suction device 20. When device 20 is shut down, it is seen that it is very easy to disengage pump assembly 40 from drive interface assembly 60, simply by rotating twist-lock flange 59 in a counterclockwise direction until twist-lock tongues 59a match with tongue receiving slots 63a in twist-lock plate 61. Once tongues 59a are aligned with slots 63a, twist-lock flange 59, and therefore pump assembly 40, can be removed vertically from twist-lock plate 61.

Figure 8:
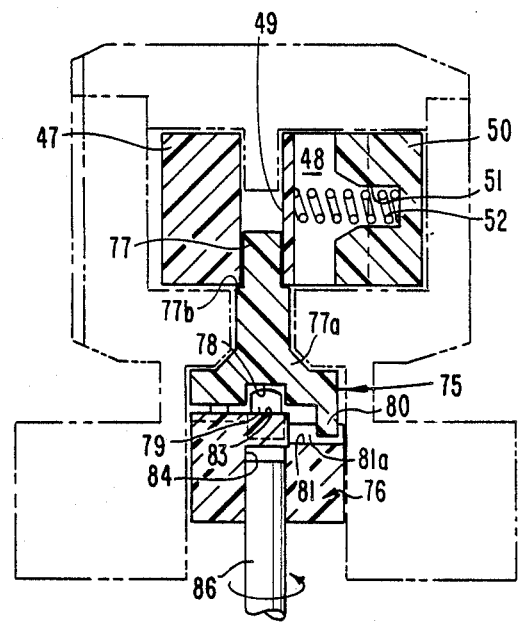
FIG. 8 is a cross-sectional view taken as shown in FIG. 6 showing the rotating components of the two assemblies.
Figure 9:
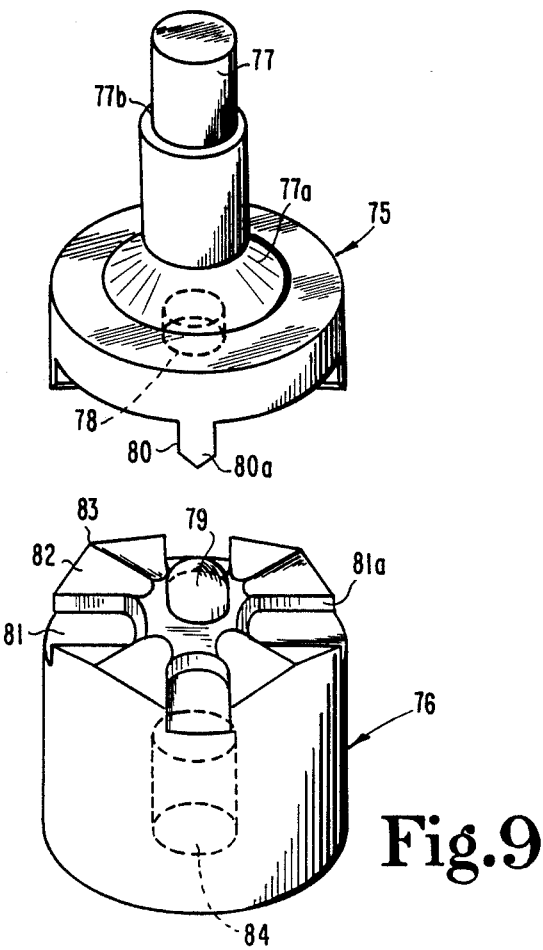
FIG. 9 is an enlarged exploded perspective view of the rotor interface and the drive interface of the drive interface assembly shown in FIG. 5.

While twist-lock flange 59 and twist-lock plate 61 provide means for easy engagement and disengagement of pump assembly 40 from motor 85, means must be provided for transmitting rotation from output shaft 86 to pump rotor 47 that is equally easy to engage and disengage. Rotor interface 75 and drive interface 76 perform such a function. Attention is now drawn to FIGS. 8 and 9 in which the details of rotor and drive interfaces 75 and 76 are illustrated. Drive interface 76 includes output shaft mating bore 84 into which output shaft 86 of motor 85 is press-fit. The top surface of drive interface 76 is contoured, as illustrated in FIG. 9, and includes several drive detents 81. In the preferred embodiment, there are four drive detents 81 spaced at 90° intervals on the top surface of drive interface 76. Drive detents 81 are recessed to provide drive surfaces 81a. Rotor interface 75 includes several drive tabs 80 projecting from the bottom of rotor interface 75 Drive tabs 80 are situated and sized to be received within drive detents 81 in drive interface 76 When drive interface 76 is rotated by motion from output shaft 86, drive surfaces 81a in drive detents 81 contact drive tabs 80 to transmit rotational motion into rotor interface 75.

Rotor interface 75 includes spindle 77 projecting from the top of rotor interface 75. Rotor 47 of pump assembly 40 includes a positioning bore 49 therethrough that is adapted to be press-fit over spindle 77 thereby providing a path for rotational motion from motor 85 to rotor 47. Since spindle 77 of rotor interface 75 is press-fit into rotor 47 of pump assembly 40 rotor interface 75 is removed with pump assembly 40 when the pump assembly is disconnected from drive interface assembly 60. Since drive tabs 80 of rotor interface 75 are not interconnected with drive detents 81 of drive interface 76, rotor interface 75 can be disengaged from drive interface 76 by simply moving rotor interface 75 vertically away from drive detents 81.

To facilitate assembly of rotor and drive interfaces 75 and 76, a "self-aligning" feature is provided in which drive tabs 80 of rotor interface 75 include beveled portions 80a and drive interface 76 includes sloped surfaces 82. Sloped surfaces 82 slope from a crest 83 situated generally midway between adjacent drive detents 81, toward each of the adjacent drive detents. When rotor interface 75 is pressed into contact with drive interface 76, beveled portions 80a contact sloped surfaces 82 between crest 83 and drive detents 81. As rotor interface 75 is pressed further toward drive interface 76, the angles of beveled portion 80a and sloped surfaces 82 cause drive tab 80 to slide along sloped surfaces 82 into drive detents 81, which causes rotor interface 75 to rotate slightly. The interaction of beveled portions 80a and sloped surfaces 82 provide a simple and sure means of "self-alignment" to ensure that drive tabs 80 fall securely within drive detents 81 and abut drive surfaces 81a.

At the center of the top surface of drive interface 76, there is provided an alignment knob 79 that is adapted to be received within alignment recess 78 of rotor interface 75. The interaction of alignment recess 78 and knob 79 ensures that rotation from drive interface 76 is transmitted to rotor interface 75 along the longitudinal rotational axes of each of the interfaces. The presence of alignment recess 78 and knob 79 prevent misalignment of the respective interfaces which could result in uneven rotation of rotor interface 75 or drive interface 76. Uneven rotation can result in wear on either of these parts or in binding of pump rotor 47 during rotation.

In the assembly of drive interface assembly 60, motor spacer 62 is mounted on motor 85. Motor space 62 includes several first mounting screw bores therethrough, each of the bores aligned over mounting holes 85a in motor 85. Each of the first mounting screw bores 72 are countersunk so that first mounting screw 73 can be inserted therein and recessed from the interface surface 62a of motor spacer 62. Motor spacer 62 also includes several cooling bores 70 therethrough for convection cooling of motor 85 during operation. Twist-lock plate 61 is mounted atop motor spacer 62 by second mounting screw 68 passing through countersunk second mounting screw bore 67 in twist-lock plate 61, the second mounting screws being engaged in threaded mounting bores 71 in motor space 62. Twist-lock plate 61 also includes several cooling vents 66 that are aligned generally over cooling bores 70 in motor spacer 62, to provide a convection path from cooling bores 70 to the atmosphere. The vents are also oriented to reduce the possibility of fluid entry into the motor, while maintaining sufficient convection cooling.

Once motor spacer 62 and twist-lock plate 61 have been affixed to motor 85, drive interface 76 can be pressed onto output shaft 86. When pump assembly 40 is assembled, as will be discussed in more detail later, rotor interface 75 is inserted through spindle interface bore 57 in pump body 41, as shown in FIGS. 6 and 8. In pump body 41, spindle interface bore 57 communicates between pump chamber 46 and drive interface cavity 58. Drive interface cavity 58 is formed at the interior of twist-lock flange 59. Motor spacer 62 includes a drive interface bore 69 aligned with drive interface cavity 58. As illustrated in FIG. 8, rotor interface 75 and drive interface 76 engage generally within drive interface cavity 58 and drive interface bore 69 when pump assembly 40 and drive interface assembly 60 are finally assembled.

Spindle interface bore 57 includes a chamfered portion 57a that corresponds to beveled bearing surface 77a of rotor interface 75, as shown in FIGS. 8 and 9. Chamfered portion 57a and beveled bearing surface 77a provide a smooth bearing region during the rotation of rotor interface 75. The angled surfaces of chamfered portion 57a and beveled bearing surface 77a prevent binding of the rotating components, particularly when subject to axial thrust from either rotor 47 or motor 85. The interaction of chamfered portion 57a and beveled bearing surface 77a also helps seal pump chamber 46 during operation of portable medical suction device 20. With spindle 77 projecting through spindle interface bore 57 and into pump chamber 46, positioning bore 49 is solvent bonded onto spindle 77. Rotor 47 is not pressed so far onto spindle 77 as to cause rotor 47 and rotor interface 75 to bind within pump body 41. proper spacing between the rotor and the pump body is insured by step 77b midway along the length of spindle 77. During assembly, rotor 47 is slid onto spindle 77 until it contacts step 77b, as shown in FIG. 8.

Figure 10:
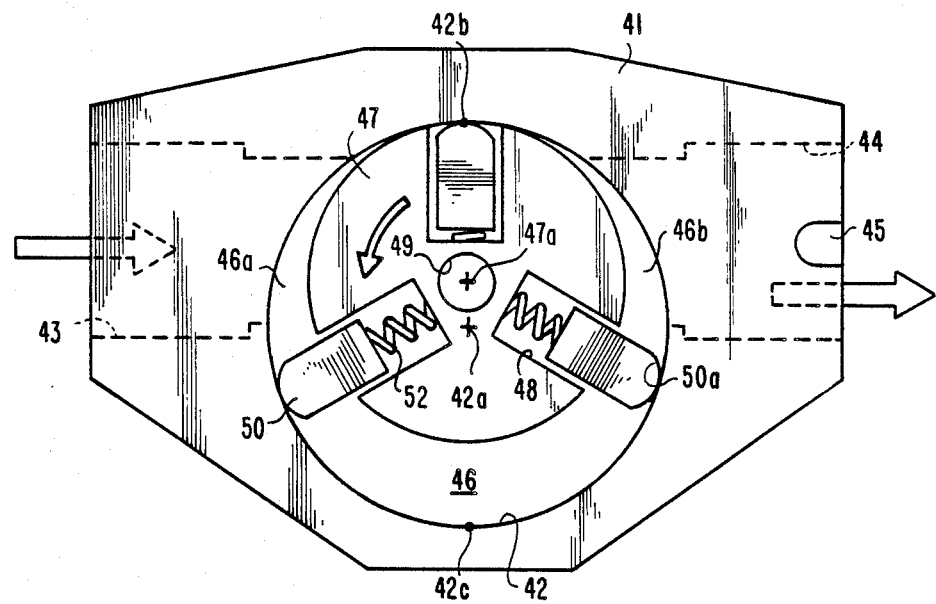
FIG. 10 is an enlarged top view of the pump assembly without the pump cover engaged, as viewed in the direction the arrows along the line 10—10 in FIG. 5.

The construction of pump assembly 40 is illustrated with reference to FIGS. 6, 8 and 10 The pump assembly 40 includes pump body 41 and pump cover 53. Pump body 41 comprises a rotor bore 42 forming a pump chamber 46. As previously noted, pump chamber 46 communicates with spindle interface bore 57. Pump body 41 includes an inlet opening 43 and an outlet opening 44 through the body and communicating with pump chamber 46. As shown in FIG. 10, the axis of inlet and outlet opening 43 and 44 do not pass through the axis 42a of rotor bore 42, for reasons that will be described herein. Pump body 41 also includes a cover locating notch 45 into which locating tongue 54 on pump cover 53 fits when the cover is mounted atop the pump body. Pump cover 53 includes a mounting pad 55 that is adapted to seat snugly within rotor bore 42 of pump body 41 to provide a sealing surface. When pump assembly 40 is finally assembled, pump cover 53 is solvent bonded onto pump body 41 to provide a leakproof seal.

Before pump cover 53 is installed however, rotor 47 is placed within pump chamber 46 mounted on spindle 77 as previously described. It will be noted from FIG. 10 that the axis 47a of rotor 47 is offset from rotor bore axis 42a. When pump assembly 40 and drive interface assembly 60 are completely constructed, rotor axis 47a extends vertically through rotor 47, spindle 77 of rotor interface 75, drive interface 76, output shaft 86, twist-lock flange 59, twist-lock bore 63 in twist-lock plate 61, drive interface bore 69 and motor spacer 62. With rotor axis 47a offset from rotor bore axis 42a, rotor 47 has a point of closest approach to rotor bore 42 at the location designated 42b in FIG. 10. Point of closest approach 42b is situated generally midway between inlet and outlet openings 43 and 44. Point of farthest approach 42c to rotor bore 42 is 180 degrees opposite point of closest approach 42b.

Rotor 47 comprises several vane slots 48 extending from top to bottom in rotor 47. Positioning bore 49 extends centrally through rotor 47. As well as providing an interface for solvent bonding to spindle 77, positioning bore 49 also provides a bearing surface within which rotor bearing pin 56 resides. Rotor bearing pin 56 lies along rotor axis 47a, and acts as a reaction pin to ensure steady rotation of rotor 47 during operation to prevent binding of pump assembly 40. Pump body notch 45 and pump cover locating tongue 54 ensure that pin 56 is properly aligned along rotor axis 47a during assembly. Even a slight misalignment of cover 53, and therefore pin 56, will produce a misalignment of rotor 47, leading eventually to uneven wear and premature failure of pump assembly 40.

Vanes 50 fit into vane slots 48, and include a spring bore 51 within which a biasing spring 52 is seated. As rotor 47 rotates, centrifugal force causes the vanes to slide radially within vane slots 48 as is typical in rotary vane pumps. Biasing spring 52 acts against vane slot 48 to push vane 50 outward from rotor axis 47a. When a vane is situated at point of closest approach 42b, biasing spring 52 is fully compressed within vane slot 48 by vane 50. When vane 50 is at point of farthest approach 42c, biasing spring 52 is nearly completely extended. Biasing spring 52 acts to ensure that vane 50 seals tightly against rotor bore 42 during operation of portable medical suction device 20. The use of biasing springs 52 allows the rotational speed corresponding to a certain suction and flow rate to be minimized. The amount of suction generated depends, to a certain degree, on the seal between vanes 50 and rotor bore 42. During rotation of the rotor 47, the vane-to-bore seal is maintained by centrifugal action on the vanes. With assist from the biasing springs 52, less centrifugal force is required to produce the same vane-to-bore seal; therefore, the rotational speed can be reduced, which, in turn, reduces the motor and electrical requirements for the suction device. Vane 50 includes a curved end 50a that contacts rotor bore 42. The radius of curvature of curved end 50a is less than the radius of rotor bore 42, thus ensuring solid contact between vane 50 and rotor bore 42, even if the vane is slightly cocked within vane slot 48.

The orientation of inlet and outlet openings 4 and 44, respectively, and rotor 47 within rotor bore 42 is different from the rotary pumps heretofore known in the prior art. Referring again to FIG. 3, it is seen that in prior art rotary pumps, the inlet and outlet openings are nearly adjacent. In these prior art pumps, the inlet and outlet openings are at the narrowest portions of the pump chamber, since they are immediately adjacent the point of closest contact of the rotor to the rotor bore. Furthermore, in the case of the typical triple-vane rotary pump, the inlet and outlet openings can both fall entirely within the rotating cavity formed between adjacent vanes. In the rotary pump of the present invention, however, the inlet and outlet openings are nearly diametrically opposite each other. The inlet and outlet openings intersect the pump chamber 46 at vacuum portion 46a and pressure portion 46b, respectively. Since the openings 43 and 44 are remote from the point of closest approach 42b, a larger flow path is created between the openings and the pump chamber than in the prior art devices. Furthermore, under no possible orientation of rotor vanes 50 can inlet opening 43 and outlet opening 44 be fully contained within the rotating cavity formed between adjacent vanes. In a large part, the design of prior art rotary vane pumps used in medical suction devices is dictated by the use of the rotary pump solely as a vacuum source, rather than as a "flow-thru" device. Thus, the motivation behind the rotary pump design of the present invention did not exist for the prior art pumps, that is to enlarge the flow path to accommodate particles and foreign substances present in aspirate.

This arrangement of rotor and inlet/outlet openings within pump body 41 of the present invention is an important feature to the "flow-thru" characteristics of the rotary pump. Referring to FIG. 10, as a lead vane 50 passes inlet opening 43 a vacuum is formed in vacuum portion 46a of pump chamber 46. This vacuum draws aspirate from the patient by way of suction. As rotor 47 continues to rotate, the adjacent trailing vane, positioned at point of closest approach 42b in FIG. 10, advances toward and beyond inlet opening 43 to form a rotating cavity filled with aspirate. The centrifugal and spring forces acting on the lead and trailing vanes seal the rotating cavity as the pump rotates. In addition, the bearing action of the vanes on rotor bore 42 serves a self-cleaning function to keep the rotor bore smooth during operation of suction device 20.

As rotor 47 continues to rotate, the aspirate-filled rotating cavity passes by the point of farthest approach 42c. When the lead vane reaches outlet opening 44 slightly beyond point of farthest approach 42c, the contents of the rotating cavity are compressed only slightly. As the pump continues to rotate, a pressure head is generated at outlet opening 44 by the trailing vane, expelling aspirate through the outlet opening. This pressure head also serves to slightly inflate the reservoir bag during operation of portable medical suction device 20. The inflation of reservoir bag 120 is desirable to ready the bag for collection of the aspirate. With the bag slightly inflated, the aspirate collects in the bottom of reservoir bag 120.

The operation of the present rotary pump is more efficient than the prior art rotary pumps, at least when used in a "flow-thru" application, since the vacuum portion 46a into which the aspirate is pulled by suction is larger than the initial vacuum portion of the prior art rotary pumps. Another advantage is that there is considerably less compression of the aspirate occurring in the present pump as opposed to the prior art rotary pumps in which the outlet opening is directly adjacent the point of closest approach of the rotor to the rotor bore. The rotary pump of suction device 20 is generally more energy efficient since the aspirate is only transported about 180° from inlet opening 43 to outlet opening 44. In the prior art devices, such as the peristaltic pumps, the aspirate travels about 350° from inlet to outlet. Furthermore, the orientation of the inlet and outlet openings in the present invention reduces "pump down" time —i.e., the time required for the proper vacuum to be attained at the patient end of the suction tube. The "pump down" time is further reduced in the present invention, relative to most of the prior art devices, since it is not necessary to evacuate the collection container before vacuum is attained in the suction tube.

In the present embodiment, the motor spacer 62 the twist-lock plate 61, and the drive interface 76 are composed of acetal plastic, such as that sold under the tradename Delrin. Pump body 41, pump cover 53, rotor interface 75 and rotor 47 are composed of clear acrylic, while the vanes are formed from polypropylene. In the present invention, the components of the pump assembly 40 and the rotor interface are adapted to be disposable, and therefore are formed from an inexpensive yet durable material. Since the present medical suction device 20 is intended to be portable, the elements of pump assembly 40 are made as small as possible, while still retaining the requisite performance characteristics for a device of this type. Thus, rotor bore 42 is, in applicant's preferred embodiments to date, about 0.937 inches in diameter. Pump rotor 47 has a diameter of 0.750 inches. Rotor axis 47a is offset from rotor bore axis 42a by about 0.094 inches. Thus, rotor 47 contacts rotor bore 42 at the point of closest approach 47b. In rotor 47, vane slots 48 have a radial depth of about 0.27 inches, which is the same dimension as the length of rotor vane 50. Thus, vane 50 can be depressed flush with the outer surface of rotor 47 at the point of closest approach 47b. Spring bore 51 within vane 50 is about 0.21 inches deep, so that when vane 50 is completely depressed within vane slot 48, biasing spring 52 has a compressed height of 0.21 inches. The biasing springs 52 have a free length of 0.562 inches and a spring rate of 0.77 lbs./in. The springs are composed of standard steel music wire and are gold-iridium plated for corrosion resistance. It can be noted that springs 52 are the only metallic elements of the disposable suction component.

At the point of farthest approach 47c, the vane 50 projects about 0.1875 inches beyond the rotor 47, and biasing spring 52 then has a length of about 0.3975 inches measured from the interior of vane slot 48 to the end of spring bore 51 in vane 50 Inlet bore and outlet bore 43 and 44, respectively, have a thru diameter of 0.37 inches, with a countersunk diameter of 0.39 inches to accept standard vinyl medical tubing. The vinyl suction tube 22 is solvent bonded into the countersunk portion of inlet opening 43, while the vinyl collection tube 23 is similarly solvent bonded into outlet opening 44.

Pump assembly 40 is fully constructed and sealed prior to use by medical personnel. Thus, rotor bore 42 is lubricated prior to solvent bonding pump cover 53 onto pump body 41. The lubricant used in the preferred embodiment of the present invention is a mixture of a non-toxic high grade medical silicone oil and a non-toxic teflon gel. The silicone oil provides lubrication and is an anti-foaming agent to prevent foaming of the aspirate within pump body 41 during high speed agitation and within the reservoir bag 120 (which reduces the available volume). The teflon gel provides lubrication in the form of a plating action. Since the suction components of portable medical suction device 20 are intended to be disposable, there is no need for a continuous oil supply as used in prior art suction devices, particularly those employing a rotary vane pump.

In another embodiment of the present invention, the rotor bore 42 is frosted to provide a plurality of recesses, or interstices. When rotor bore 42 is lubricated, certain amounts of the lubricant are trapped within these interstices. During operation of portable medical suction device 20, the passage of the rotor vanes 50 along rotor bore 42 tends to erode the surface of rotor bore 42. As the surface of rotor bore 42 is worn away, the interstices formed in the frosted surface are eroded away and the lubricant contained within the interstices is released. Thus, the frosted surface of rotor bore 42 provides a continuous source of lubrication during the use of the portable medical suction device 20. The presence of the continually released lubricant can extend the life expectancy of the disposable pump system to about 3 hours, while the typical duration of use is not expected to exceed 1.5 hours total to a patient. Thus, while the use of degradable materials, such as acrylic and propylene renders the suction components economically disposable, the use of the frosted rotor bore 42 extends the functional life of pump assembly 40 well beyond the period of time normally expected for operation of suction devices of this kind. The polypropylene material of the vanes is softer than the acrylic of the rotor bore, so the vanes will wear more rapidly. The surface of rotor bore 42 wears more slowly to allow access to more oil. Vanes 50 must be relatively softer to conform to rotor bore 42 in order to provide adequate sealing during operation. As the vanes wear, filaments from the vanes act as a wick to draw lubricant from the vane bore interstices.

Figure 11:
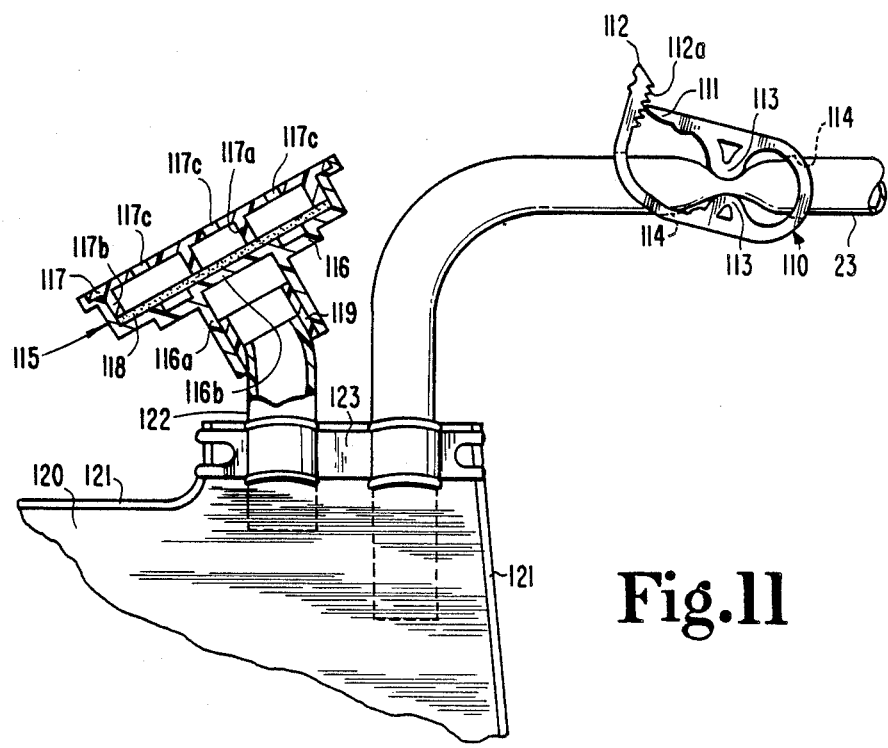
FIG. 11 is an enlarged fragmentary side view of a portion of the reservoir bag, collection tube and tube clamp of the disposable suction component of the present suction device shown in FIG. 1, with the hydrophobic filter shown in cross-section.
Figure 12:
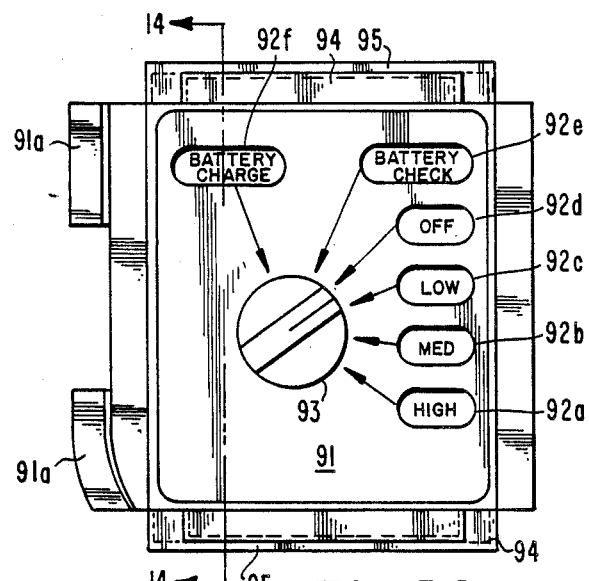
FIG. 12 is a top view of the electronic control housing shown in FIG. 1.

Between pump assembly 40 and reservoir bag 120 is a tube clamp 110 situated about collection tube 23, illustrated in FIG. 11. Collection tube 23 passes through tube receiving openings 114 in tube clamp 110. Tube clamp 110 includes a ratchet 111 that is locked in position by serrations 112a on catch 112. Tube clamp 110 also includes constriction knobs 113 that oppose each other on opposite sides of collection tube 23. During the operation of portable medical suction device 20, the tube clamp 110 is in its free state, as shown in FIG. 1. Once suctioning is complete, it is desirable to seal the contents of reservoir bag 120 to prevent any aspirate and foreign substances from flowing back through pump assembly 40 and out suction tube 22. Thus, ratchet 111 can be locked into a position by catch 112 so that constriction knobs 113 compress collection tube 23 between each other In a normal procedure, the tube clamp 110 will not be locked until the suction system has been rinsed using rinse bottle 25. Use of tube clamp 110 also allows medical personnel to seal the contents of reservoir bag 120 and out collection tube 23. Thus, reservoir bag 120 can be used to store the aspirate suctioned from the patient for later testing at the hospital or laboratory. Thus, the contents of the reservoir bag 120 can be safely carried without risk of leakage and cross-contamination. A label can be provided for the reservoir bag 120 to record patient information if the contents of the bag are to be sampled.

Reservoir bag 120 is composed of 12 mil vinyl. The bag has a burst strength of about 20 p.s.i., which is well in excess of the maximum pressure generated by pump assembly 40 (although hydrophobic filter 115 should prevent such pressure buildup unless it is occluded). The bag can be formed from two sheets of 12 mil vinyl, heat sealed along sealing seam 121, or can be formed from a single sheet that is folded over and heat sealed at the free edges in a similar fashion. Reservoir bag 120 is loosely folded when stored within support frame 30. The reservoir bag can also be composed of polyethylene in an accordion construction to expand as it is filled with aspirate. As shown in FIG. 11, collection tube 23 and filter tube 122 are heat sealed into sealing seam 123 when reservoir bag 120 is fabricated. Filter tube 122 is bonded to hydrophobic filter 115. Hydrophobic filter 115 provides an air vent for air residing within reservoir bag 120 or suctioned through pump assembly 40 and collection tube 23. Since filter 115 is hydrophobic, only air may escape through the filter, and not a liquid or other foreign substance. Thus, reservoir bag 130 is vented without risk of liquid leakage. The hydrophobic filter is necessary to vent pressure generated by pump assembly 40 that slightly inflates reservoir bag 120. Also, air may be suctioned along with solid or liquid matter from the patient. Accumulation of air in reservoir bag 120 will reduce its capacity for solid or liquid matter, thus it is necessary to vent the air or similar gas from reservoir bag 120.

Hydrophobic filter 115 includes a housing base 116 adhered to housing cover 117, each composed of styrene plastic. Housing base 116 includes an adaptor flange 116a within which sealing tube section 119 is solvent bonded. Sealing tube section 119 is solvent bonded to filter tube 122 to form a leakproof path into filter 115. Filter membrane 118 is adhered at its perimeter to housing base 116. Housing base 116 includes a plurality of support ribs 116b to support the central portion of membrane 118. In the typical hydrophobic filter 115 used in the present invention, there are eight ribs arranged in a star pattern. Housing cover includes a pair of retaining rings 117a and 117b projecting into filter 115 to retain membrane 118 and prevent it from ballooning excessively under the pressure generated by pump assembly 40. Vent openings 117c in housing cover 117 allow air passing through membrane 118 to escape into the atmosphere. Membrane 118 is composed of a woven material, typical of hydrophobic filters, forming pores sufficiently small to allow only gasses to pass through, and not solids or liquids. The pore size of the filter membrane is largely controlled by the surface tension of the liquid to be restrained. As the liquid pressure increases, the pore size must decrease to continue to act as a liquid barrier. In the preferred embodiment, a pore size of three (3) microns is adequate for membrane 118 to properly function at the operating pressures developed by pump assembly 40.

As previously described, reservoir bag 120, with hydrophobic filter 115 affixed thereon is situated at one end of support frame 30 and held in position by collection bag retaining wall 31, and sidewalls 30d and 30e. When fully retained within support frame 30 reservoir bag 120 has a volume capacity of about 450 ml. When the bag is fully expanded beyond support frame 30 through the opening in end wall 30c, the reservoir bag 120 has a capacity of about 1,000 ml.

As described above, one end of both suction tube 22 and collection tube 23 are solvent bonded to pump assembly 40. Collection tube 23 is also heat sealed at its other end into reservoir bag 120. Hydrophobic filter 115 is solvent bonded to reserVoir bag 120, and provides venting only for gasses, such as air. Thus, it is seen that the disposable suction component is entirely liquid sealed except at the patient end of suction tube 22, with one exception. As described earlier, rotor interface 75 includes beveled bearing surface 77a that rides within chamfered portion 57a of spindle interface bore 57. Silicone oil and teflon gel are applied to the porous surface of beveled bearing surface 77a and spindle 77 to provide lubrication and some sealing against chamfered portion 57a.

During operation of pump assembly 40 a vacuum is drawn in spindle interface bore 57. This vacuum prevents the leakage of air or aspirate out of spindle interface bore 57 into motor 85 or the atmosphere. However the vacuum at spindle interface bore 57 does draw a certain amount of external air through rotor spacer 62, twist-lock plate 61, and spindle interface bore 57 into pump chamber 46. This small amount of suction leakage decreases the overall suction efficiency of portable medical suction device 20, although the degradation is very minimal. A benefit of this vacuum/air flow through interface bore 57 is that lubricant at the lower areas of rotor interface 75 is drawn up to the spindle 77 and beveled bearing surface 77a to facilitate continued lubrication of these load bearing surfaces.

One key advantage of the unitary construction of the disposable suction element is that the suction device 20 is operable in any position without risk of overflowing into the electrical or metallic components of the device, provided that filter tube 122 to hydrophobic filter 115 is kept clear. Once filter tube 122 is occluded by aspirate collected in reservoir bag 120, the pressure generated by pump assembly 40 through collection tube 23 gradually increases as reservoir bag 120 begins to inflate. Once the back pressure from reservoir bag 120 reaches a threshold level, the suction produced by pump assembly 40 diminishes, although the pump rotor will continue to rotate. Once the medical personnel notices the decrease in suction at suction tube 22, it is a simple matter to investigate to determine whether reservoir bag 120 is filled with aspirate or whether the bag is improperly oriented so that filter tube 122 is occluded. In medical suction devices of the type of the present embodiment, it is important that the device be operational in a variety of positions, since in an emergency situation the medical personnel may be faced with harsh terrain or generally inaccessible areas to reach the patient. In the prior art devices, care must be continually taken to avoid misorienting the device so that aspirate can flow or leak into the pump components. Thus, most of the prior art medical suction devices are operational only so long as the device is maintained in a substantially vertical attitude. Portable medical suction device 20 of the present embodiment has no such limitation since it is operational in nearly any orientation possible.

Portable medical suction device 20 of the preferred embodiment is an electric unit, in that pump assembly 40 is driven by a high torque electric motor 85. The electrical system of the suction device 20 includes a battery 87, an electronic control assembly 90, an AC/DC converter 88 and an external DC power cable 89. The battery 87 is a 12 volt lead/acid gel-cell type rechargeable battery. Battery 87 and electronic control assembly 90 are integrated into a single unit that is serviceable only at the manufacturing level to prevent incorrect repairs or adjustments by medical technicians in the field. The gel-cell battery 87 contains a gelled electrolyte rather than liquid within the battery case, so that there is no liquid of any kind to splash around or ooze out of the battery into the adjacent components. Battery 87, then, is usable in any orientation. Since medical suction device 20 is intended to be fully portable and reusable, battery 87 is rechargeable. Another benefit of the gel-cell battery is that it is completely rechargeable with no recharging memory, such as arises in nickel-cadmium batteries. It is important that the battery be capable of nearly 100% recharging so that the battery can provide sufficient energy to drive the motor during each emergency use The gel-cell battery 87 used in the present embodiment has a demonstrated capability for continuous running of up to three hours from a single charge. It should be noted, however, that given the modular construction of portable medical suction device 20, it is not unwieldy to simply remove electronic control assembly 90 and battery 87 as a unit and replace with a new control assembly and gel-cell battery unit in less than one minute.

AC/DC adaptor 88 is electrically connected to battery 87 through electronic control assembly 90, and is usable solely to recharge the battery. External DC power cable 89 interfaces with a vehicle DC power supply or a wheelchair battery. Battery 87 can be recharged from this external DC source. In addition, the external DC source can be used as an alternate power supply for motor 85. The ability to operate from vehicle DC power reduces the risk of loss of power to the suction device should battery 87 fail or completely discharge. External DC power cable 89 can be configured as a cigarette lighter plug. In one version of the present invention, this cigarette lighter plug is stored in support frame 30 in the space defined by access openings 32a, 29a and 33a, previously noted as dedicated to supporting rinse bottle 25. In this version, the rinse bottle is stored in a pocket in a carrying case, to be described herein.

Referring to FIG. 1, battery 87, converter 88, and motor 85 all are electrically interfaced with electronic control assembly 90 through connector 100 situated within connector channel 35 of support frame 30. Electronic control assembly 90 includes a selector switch 93 that can be rotated to select from several positions 92a–92f in housing 91. Selection can be made between positions corresponding to high 92a, medium 92b, and low 92c rotational speeds of motor 85, system shutoff 92d, battery check mode 92e, and battery charge mode 92f. At each of these positions, a descriptive translucent label is fixed in a recess in the housing and is backlighted by an LED (except for shutoff position 92d). The colors of the LED's are varied between the positions, as described herein, to provide a readily apparent indication of the mode of operation of suction device 20.

One feature of the present suction device 20 is that the electronics permits the motor 85 to be operated at three speed ranges—high, medium, low—that are important to account for variety of suction environments encountered in most medical situations. For instance, the low motor speed, indicated by a yellow LED at position 92c, corresponds to a flowrate of about 30 lpm at a vacuum of 100–125 mm Hg, which is typically necessary for gentle endotracheal or nasopharyngeal suctioning. The medium speed, designated by a yellow LED at position 92b, corresponds to a flowrate of 36 lpm and a vacuum of 200–225 mm UG. The medium speed of operation is typically used for oropharyngeal suctioning. Finally, the high speed range, indicated by a yellow LED at position 92a, corresponds to a flowrate of approximately 45 lpm at a vacuum of 375–40 Omm Hg, and would be used in emergency circumstances, such as stomach pumping and oropharyngeal suctioning of vomitus.

Most of the prior art medical suction devices provide only two speeds, high and low, that are created by changing the connection between two six or twelve volt power sources from a series to a parallel circuit. Some prior art suction devices drive the pump motor at a constant high speed and require the user to vary the vacuum using a regulator which, essentially, provides a continuously variable controlled leak. At least one device, manufactured by Rico, uses a user manipulated continuously variable motor speed control. In each of these latter types of devices, the medical technician must attempt to adjust the vacuum within acceptable ranges depending on the suction environment encountered. In an emergency medical situation, the emergency medical technician has precious little time to try to dial in the proper suction level. While devices capable of two suction levels remove the choices from the technician, they fail to provide additional discrete suction levels required in the field for the typically encountered suction requirements.

The present invention uses state of the art electronics to produce three speed ranges that are commonly required in field use of portable medical suction device 20. The electronics circuitry within housing 91 of electronic control assembly 90 are illustrated schematically in FIG. 13. Speed control circuit 130, illustrated in the schematic of FIG. 13, comprises three Darlington high power transistors, designated Q1, Q2 Q3 in standard electrical nomenclature. In the preferred embodiment, these transistors are type TIP120 devices readily available in the commercial market, such as sold by Motorola. The collector, emitter and base of all three transistors Q1–Q3 are connected at respective junctions 131–133. When selector switch 93 is in any of the positions 92a–92c, positive voltage from battery 87 is applied at collector junction 131. Battery voltage is also applied at base junction 133 through a resistance value dependent on what speed range has been selected. When the low speed 92c is selected, the battery voltage is applied across a resistor designated as R4, thereby reducing the voltage seen at base junction 133. Likewise, resistor R5 reduces the voltage at the base junction when medium speed 92b is selected. When high speed 92a is selected, no resistor is encountered in line 134, so base junction 133 sees the entire battery voltage. In the preferred embodiment, resistor R4 has a value of 3000 ohms, while the R5 value is 1000 ohms; thus, the voltage drop across the low speed resistor R4 is greater than that across the medium speed resistor R5.

Three yellow LED's, designated CR3, CR4, and CR5, are connected to switch locations 92a, 92b and 92c, respectively, in parallel with the resistors R4 and R5 and line 134 respectively. The LED's are illuminated to indicate that the low, medium or high speed range has been selected.

Emitter junction 132 is connected to the positive pole of motor 85. Current from each of the transistors Q1–Q3 combines at junction 132 and is dependent upon the base voltage applied at base junction 133. Thus, the variation in voltage seen at base junction 133, due to selection of the low, medium or high speed range, resistance values, causes a corresponding variation in current combined at emitter junction 132. The three resulting current levels drive motor 85 at three rotational speeds. Motor 85 is capable of a peak speed of about 14,000 rpm unloaded. When load is applied to motor 85 during operation of suction device 20, the actual loaded rotational speed will decrease, and even fluctuate as the amount of load fluctuates, as is common with DC motors. Motor 85 is diode protected, such as by diode D7 in FIG. 13, to prevent reverse rotation of output shaft 86. Diode D7 also absorbs voltage and current spikes generated when the motor inductive field collapses after the system is shut off, to protect the power transistors.

It is apparent that the described technology can be used to provide more than three discrete suction levels, as required by the particular application of the present suction device 20. However, the benefit over the prior art devices remains that discrete ranges of suction are provided without unnecessary and unwanted involvement by the technician during operation. It is only necessary to select the desired range of suction using selector switch 93. It should be noted that, while a similar result may be accomplished by a resistor network alone, the power requirements of suction device 20 necessitate the use of large power resistors. These power resistors are much larger than the Darlington transistors selected for this device and, consequently, would require a larger electronic control housing. Moreover, the power resistors are less efficient in dissipating generated heat than the transistors Q1-Q3. Finally, power resistors introduce inductance and are generally unable to stabilize the electronic control system, while transistors Q1-Q3 tend to smooth out voltage and current spikes to keep the motor speed and pump flow rate within the expected ranges.

When selector switch 93 is placed in the battery check mode at location 92e, a resistance load is placed across rechargeable battery 87. Battery check circuit 136 includes a zener diode CR1 in a voltage divider network comprising resistors designated R1 and R2. If zener diode CR1 sees sufficient voltage from the battery, current will flow through the diode and through resistor R3 and illuminate the green LED CR2, situated at location 92e, to indicate adequate charge. A partial depletion of the battery capacity will cause LED CR2 to be dimly lit. As the battery is further depleted, insufficient voltage will be applied to the zener diode CR1, current will not flow through the diode and the green LED CR2 will not light.

Selector switch 93 can also be placed in the battery charge mode, at position 92f, in which rechargeable battery 87 can be recharged by means of a standard AC wall outlet or a DC vehicle power supply. Red LED CR6 located in battery charge circuit 140 is illuminated when external electrical power is provided to either AC/DC converter 88 or external DC power connector 89. Illumination of the red LED CR6 acts as an indicator to the medical operator that the device 20 is connected to an external power source, whether or not recharging is actually being performed. Thus, the operator will be able to prevent accidental damage to AC/DC converter 88 or DC power connector 89 that might occur when attempting to transport the device while still connected to an external power source.

When the red LED CR6 is illuminated, recharging begins when selector switch 93 is positioned to location 92f. In the preferred embodiment, AC/DC converter 88 accepts a 115 volt AC input and converts it to an 18 volt 500 milliamp DC output. If recharging is accomplished via AC/DC converter 88, voltage regulator U1 in battery charge circuit 140 controls the charge voltage applied to battery 87 to ensure that the battery is consistently charged to its maximum potential and at the optimum voltage. Variable resistor R7, between voltage regulator U1 and the negative terminal of battery 87, controls the charging voltage, which is pre-set to 13.8 volts +/- 0.18 v during manufacture of suction device 20 to ensure optimum recharging capability. A slow blow 1 amp fuse F1 between AC/DC converter 88 and voltage regulator U1 protects the battery charge circuit 140 and battery 87 against overcurrent.

Recharging can also be accomplished from an external DC source, such as a 14 volt vehicle power source typical in emergency or other vehicles. External DC power connector 89 interfaces through battery charge circuit 140, although voltage regulator U1 is bypassed for obvious reasons. If the charge in battery 87 is sufficiently depleted DC power supplied at connector 89 can be used, alternatively, as an external source of power to motor 85 by placing selector switch 93 in any of the operating positions 92a-92c. In the operational mode, DC current from a 14 volt source passes through power diodes D1 and D2. A voltage drop of 0.6-0.7 volts across each of these diodes reduces the voltage seen by the motor to approximately the voltage generated by battery 87.

Figure 13:
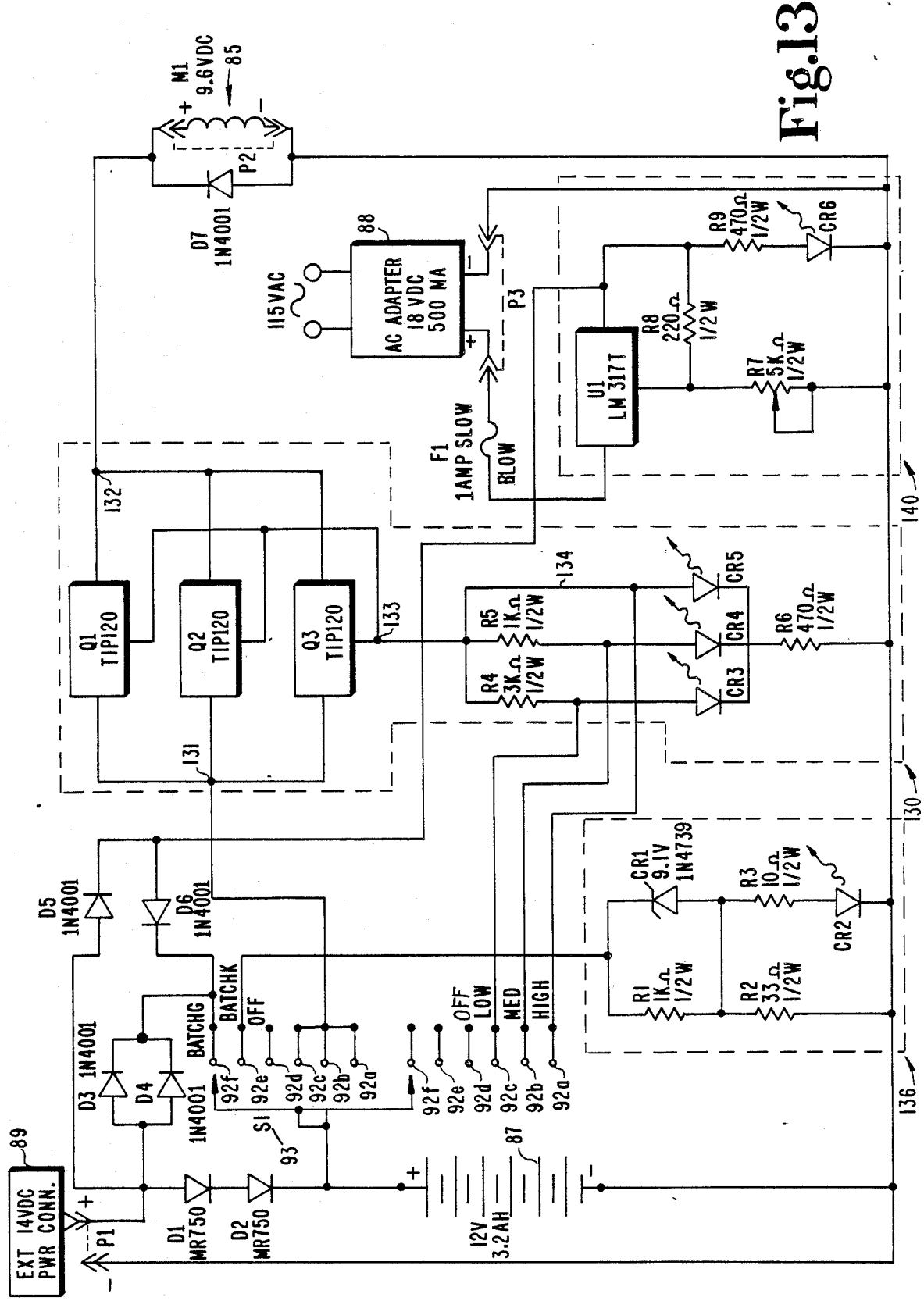
FIG. 13 is an electrical schematic diagram of the electronic circuit in the electronic control assembly for the portable medical suction device of the present invention.

The battery and circuits of electronic control assembly 90 are protected with diodes designated D1-D7 in FIG. 13 to avoid the dangers of improper polarity or shorts in the external power sources that might damage suction device 20, or at least prevent it from operating properly. Connector plug 100 integrates the mating plugs for the various electrical components of suction device 20. In FIG. 13, plug P1 interfaces with external DC power connector 89, plug P2 is associated with motor 85, and plug P3 accepts AC/DC converter 88. Connector plug 100 is uniquely configured so that there is virtually no danger of improperly inserting any of the plugs P1-P3.

Figure 14:
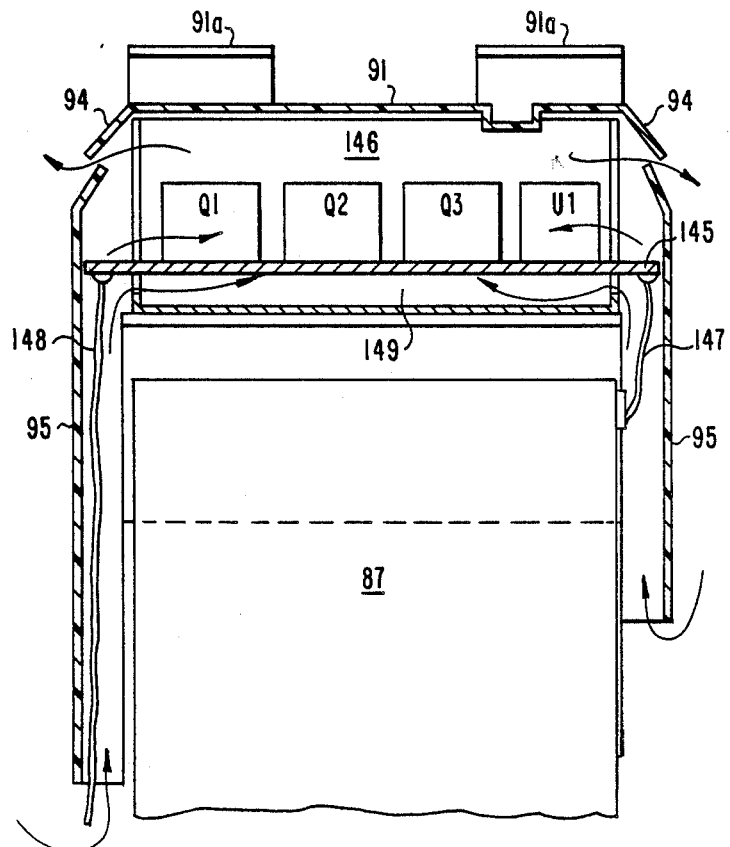
FIG. 14 is a partial cross-sectional view of the electronic control assembly for the preferred embodiment taken along line 14—14 in FIG. 12 and viewed in the direction of the arrows, showing the convection flow path of cooling air through the assembly.
Figure 15:
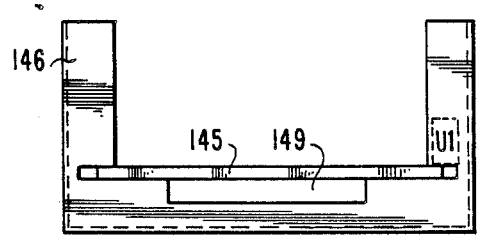
FIG. 15 is an end view of the heat sink and circuit board components of the electronic control assembly shown in FIG. 14.

The electrical components described with reference to the circuit diagram in FIG. 13 are contained within housing 91 (FIG. 1). Housing 91 is composed of polypropylene for stress and impact resistance. Referring to FIG. 14, a cross-section of electronic control assembly 90 shows the electrical components mounted on circuit board 145. Circuit board 145 is mounted on aluminum heat sink 146 as shown in FIGS. 14 and 15. Battery cables 147 extend from one end of circuit board 145 to connect electronic control assembly 90 to battery 87. External cables extend from the other end of the circuit board and terminating in plugs P1-P3, integrated in connector 100, corresponding to the external DC power source, motor and AC/DC converter.

The heat generating components, namely transistors Q1-Q3 and voltage regulator U1 (FIG. 13), are mounted on heat sink 146 to allow heat produced by these components to be rapidly dissipated. Cooling is accomplished by means of convection through two louvered vents 94 and two intake vents 95 on opposite ends of electronics housing 91. Cooling air flow enters through intake vents 95, as shown by the heavy arrows in FIG. 14. The cooling air follows intake vents 95 and passes over circuit board 145 and the heat generating components. Cooling air also travels underneath circuit board 145 through cooling channel 149. This air passing over the circuit board and components convectively carries the heat generated by the components out vents 94 to the atmosphere.

Figure 16:
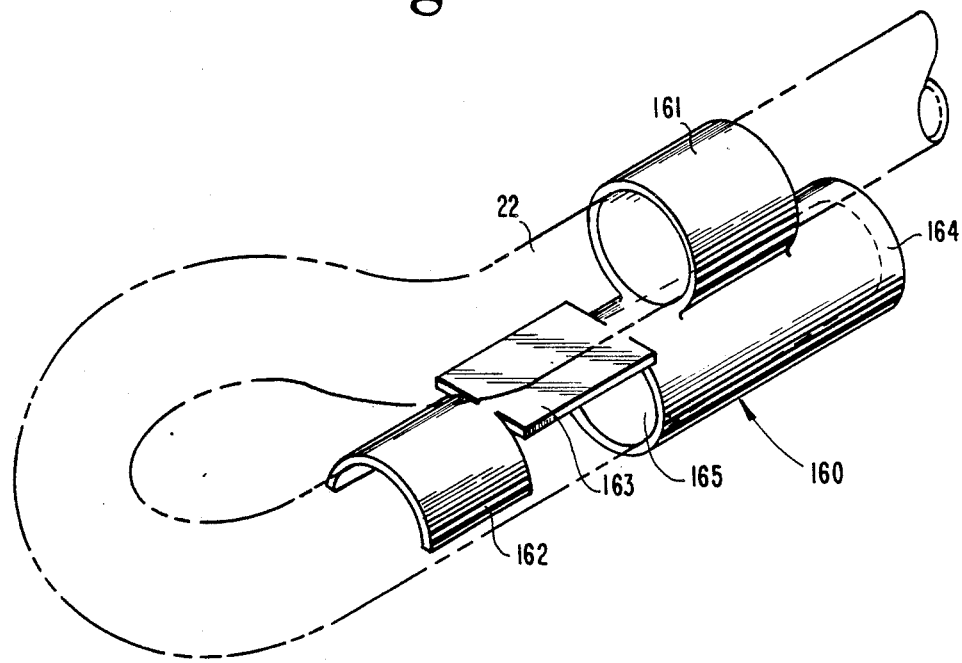
FIG. 16 is an enlarged perspective view of the tube retainer for use with the suction device of the preferred embodiment, with the suction tube shown in phantom.

Another feature of suction device 20 is a polypropylene tube retainer 160 mounted near the end of suction tube 22, as shown in FIG. 1. Referring to FIG. 16, tube retainer 160 includes a hollow tube collar 161 that is sized to fit tightly around suction tube 22. Tube collar 161 is integral with a receiver barrel 164 that is open at one end to form a tapered retainer cavity 165. Retainer cavity 165 is sized to snugly receive the end of suction tube 22 therein. Strut 163 projects from receiver barrel 164 and is formed at its cantilevered end into clamp 162. Clamp 162 is semicircular and has a diameter slightly smaller than the diameter of tube 22 so that the tube can be held in position when pressed into clamp 162.

In the use of tube retainer 160, suction tube 22 is fed through tube collar 161 either before or after use of suction device 20. After suctioning is complete and the suction elements have been rinsed, tube 22 is bent back upon itself, as shown in phantom in FIG. 16. The end of the tube is inserted into retainer cavity 165 in retainer barrel 164 and the tube is pressed into clamp 162 to hold the tube in the position shown in FIG. 16. The benefit of this tube retainer is that it provides an additional safeguard against cross-contamination from aspirate remaining in suction tube 22 after the suction device has been used. The end of the suction tube is essentially sealed within retainer cavity 165 to prevent leakage from the tube. The interaction of tube collar 161, clamp 162 and the bend in tube 22 keeps the tube retainer in position so that there is little risk of the end of the tube pulling free of retainer barrel 164.

Figure 17:
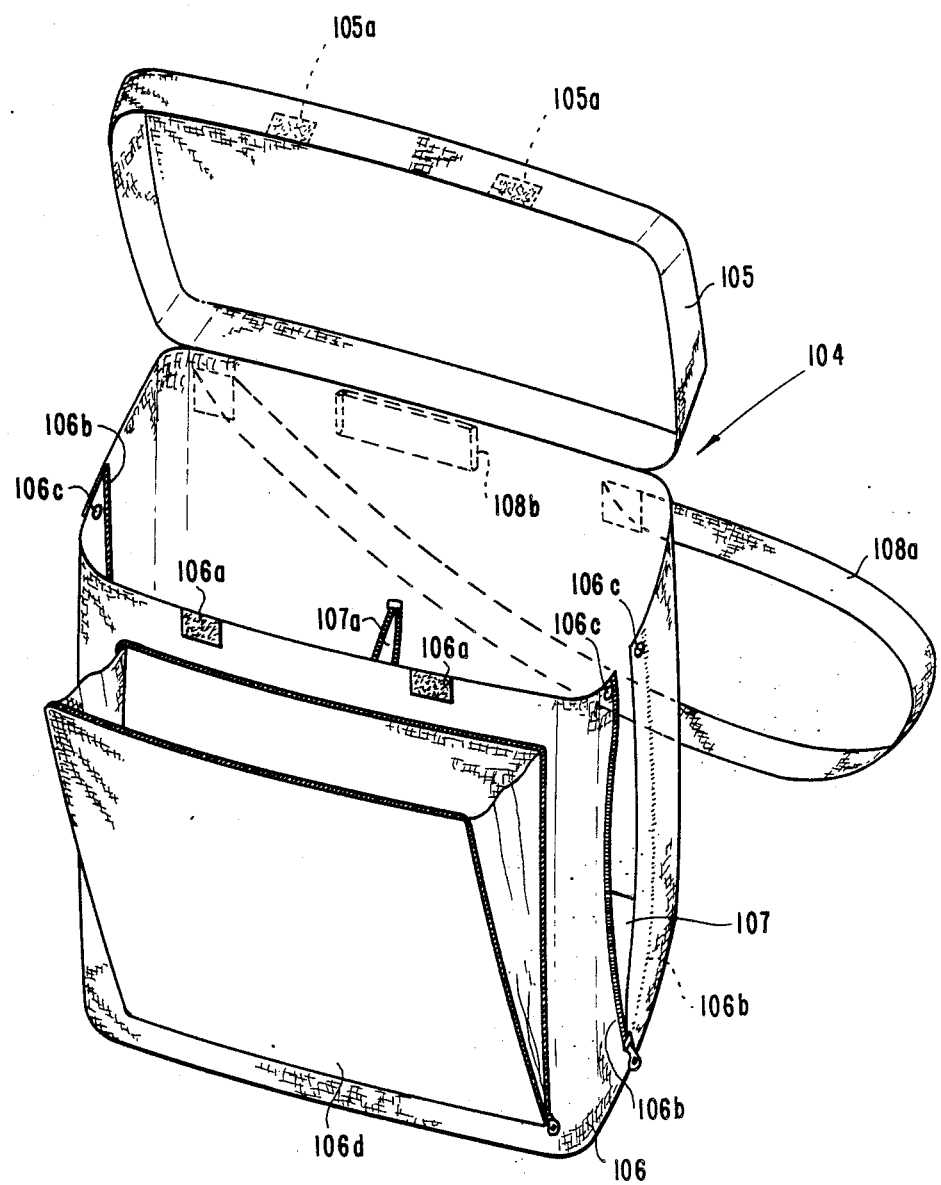
FIG. 17 is a perspective view of the carrying case for housing the suction device of the present invention illustrated in FIG. 1.

The entire portable medical suction device 20 is housed in a padded Cordura (TM) carrying case 104, illustrated in FIG. 17. The case is sized to snugly receive support frame 30 within, with all the components of suction device 20 situated within the support frame. Carrying case 104 includes a top 105, a peripheral wall 106, and a bottom 107, pressure-adhesive strips 105a and 106a, such as sold under the trademark Velcro, are utilized to close top 105 over peripheral wall 106. A carrying strap 108a is mounted at one portion of peripheral wall 106 for carrying the case over-the-shoulder. A belt loop 108b is also included to be fed onto the belt of the medical technician to keep the suction device handy at the technician's side.

In the present embodiment, peripheral wall 106 includes zippered opening 106b at both sides of carrying case 104. When support frame 30 is inserted into the carrying case, the frame is oriented so that collection bag retainer wall 31 is adjacent either of the zippered openings 106b, depending on the preference of the medical technician. When it is necessary to expand reservoir bag 120 through the opening in end wall 30b of the support frame, the bag can be extended through zippered opening 106b. Zippered opening 106b extends to the top of peripheral wall 106 to allow the wall to be folded back from the opening when it is necessary to remove an aspirate-filled reservoir bag. A snap catch 106c at the top of each zippered opening 106b can be included to prevent the case from opening completely prior to removal of the reservoir bag.

Bottom wall 107 includes a second zippered opening 107a that allows access to AC/DC adaptor 88 and external DC power cable 89 through access opening 37 in support frame 30. Second zippered opening 107a can also continue into a portion of peripheral wall 106 to improve the accessibility of the suction device external power components. An expandable zippered pocket 106d is included on peripheral wall 106 to store patient airways, catheters, additional disposable components and a user instruction card. If the rinse bottle 25 is not housed in support frame 30, a separate pocket or elastic loop can be provided within expandable pocket 106d for the bottle.

Carrying case 104 is constructed of rugged Cordura (TM) material to protect suction device 20 from abrasion and excessive moisture. The zippered openings provide ready access to the replaceable components of the modular device and the pockets allow storage of equipment inevitably required wherever the device is in operation. Each of the zippered areas are equipped with flaps over the zippers to reduce the penetration of moisture into the interior of carrying case 104. The case material and padding provide some sound insulation to reduce the noise during operation of the suction device.

The initial construction and assembly of portable medical suction device 20 is intended to provide a reliable modular device that is easily manipulated by the medical technician working in the field. In the assembly of pump assembly 40, the first step is to apply silicone oil, such as manufactured by Dow Corning, and teflon gel to the bearing surfaces of rotor interface 75. The rotor interface is then inserted into spindle interface bore 57 of pump body 41. The rotor bore 42 is lubricated with silicone oil and teflon gel, and the vane slots 48 in rotor 47 are lubricated with oil. The rotor springs 52 and vanes 50 are assembled in the rotor, and the rotor is inserted into rotor bore 42 while the vane springs are maintained depressed within the spring bores 51. Rotor 47 is slipped onto spindle 77 of the rotor interface 75 until it hits stop 77b. A drop of methylene chloride solvent is inserted at the rotor/rotor interface joint and the rotor is twisted slightly to distribute the solvent. After curing for about ten minutes, the rotor is solvent bonded to the rotor interface within the pump body 41.

The next step is to apply silicone oil and teflon gel to the underside of pump cover 53, particularly at the rotor bearing pin 56. The cover is solvent bonded to the pump body using methylene chloride solvent after clamping and curing for about ten minutes. Suction tube 22 and collection tube 23 are solvent bonded using methylene chloride to the inlet and outlet openings 43 and 44, respectively, in pump body 41. Vacuum, pressure and performance testing are performed on the pump assembly at this point.

In construction of reservoir bag 120, methyl-ethyl ketone solvent is applied to sealing tube section 119 which is bonded to filter tube 122 after curing for approximately five minutes. Hydrophobic filter 115 is affixed to sealing tube section 119 using methylene chloride solvent. It should be noted that filter tube 122 and collection tube 23, mentioned above, have previously been heat sealed into the construction of reservoir bag 120, pressure testing with the filter output occluded, is performed after the solvent bonds have cured.

Electronic control assembly 90 is constructed by installing circuit board 145 into heat sink 146, which is then installed into control housing 91. Battery cables 147 from battery 87 are soldered onto the circuit board. Charge voltage of 13.8 v is applied to the system to adjust the charge voltage at battery charge circuit 140 to 13.8 volts. Once adjusted, electronic control assembly 90 is installed onto battery 87 and into support frame 30, ensuring that latches 96 lock onto latch interface edges 97.

In the next assembly step, motor spacer 62 is mounted on motor 85 and twist lock plate 61 is affixed to the motor spacer. Drive interface 76 is pressed onto output shaft 86. The motor is installed through openings 32a, 29a and 33a in support frame 30 and the motor power cable is plugged into connector 100 situated within connector channel 35. AC/DC adaptor 88 and external DC power cable 89 are plugged into connector 100 and placed in support frame 30 through AC/DC converter access opening 37. The completed modular suction device is then placed in carrying case 104. The disposable components, solvent bonded in a unitary construction in previous steps, can then be twisted onto twist lock plate 61 as described in detail within this specification.

A variety of tests are performed on the completely assembled unit to insure reliability of the components and to gauge compliance with the Jems, ECRI and ASTM standards. In particular, tests are performed for current leakage, motor loading, battery run-down, battery check, battery charge, motor speed versus vacuum and flow, and system burn-in and verification.

The portable medical suction device 20 of the present invention represents a key advance in devices of this type, particularly in view of the reduced danger of cross-contamination of medical personnel afforded by the device. As is clear from the foregoing, any component that will contact aspirate of a patient during suctioning is completely disposable and the unitary construction nearly eliminates the risk of accidental exposure to the suctioned material. The unique configuration of the disposable component makes it extremely economical to discard after each use, rather than cleansing the potentially contaminated components as required in the prior art devices. The all-plastic construction not only contributes to the economically feasible disposability of the suction components, it also greatly reduces the weight and size of the present suction device compared to the prior art devices.

In spite of the minimal weight of the suction device of the present invention, this device has generated a suction flow rate of over 45 liters/minute in preliminary testing, which is higher than any device known to applicant and is more than twice the flow rate of the majority of the prior art medical suction devices. Due to the unique application of a rotary vane pump as a flow-through device, the present invention is capable of achieving a vacuum of 300 mm Hg in less than one (1) second, quicker than any other known device and much less than half the pump-down time of the average portable medical suction unit. Higher flow rate and quicker pump-down time can be a life-saver in field use of this device Moreover the present invention is capable of producing these statistics in virtually any orientation provided the hydrophobic filter is not occluded, with virtually no danger of leakage or overflow. The prior art devices require the use of cumbersome and expensive filters and overflow containers and are generally limited to operation in an upright orientation only. Prior art devices using a peristaltic pump, such as the Rico CMP-Battery unit described in the "Health Devices" article cited above, do not require in-line filters to protect the motor and electrical components. However, these types of devices are heavier and larger than the suction device permitted by the present invention. Furthermore, peristaltic pumps require expensive pump hardware that is cumbersome and tedious to replace if treated as a disposable component. These pumps typically have slow pump-down times, and because of the nature of the peristaltic motion energy consumption is high, reducing the battery life. Moreover, the peristaltic pump tubing is restricted to particular types of materials that are limited in the liquids that can be suctioned.

Another important benefit of the present invention is its versatility. In the medical field the present suction device may be used in any area of the hospital where flammable anaesthetics are not in use, such as for treatment of ward patients, respiratory therapy, intensive and coronary care and the clinical environment. In hospital, or even home health care applications, the disposable suction component saves valuable time for health care providers since nothing in the present device requires periodic cleansing and sterilizing. Moreover, the risk of overflow or accidental leakage is virtually non-existent.

As described in detail above, this suction device is extremely well-suited for emergency medical and trauma applications. The compact, lightweight design made possible by the present invention makes the device easily maneuvered, manipulated and operated at the scene of an injury. The particular flow-through rotary vane pump arrangement of the present invention, along with the sealed unitary construction of the suction components, allows this device to be used in almost any position, which is of cardinal importance at accident sites in rough terrain. The only emergency medical suction known to applicant that approaches the portability of the present invention is the Ohmeda Emergency Suction Unit, described in the "Jems" article cited above. However, this unit cannot achieve the flow rate, pump-down time, multiple discrete vacuum ranges and total running time attributable to the present invention.

Although the foregoing description of the preferred embodiment has concentrated on an emergency medical application, the present suction device is useful in other fields where suctioning of liquids and suspensions is required. Moreover, the disposable suction component makes the present device valuable in situations where hazardous or contaminated materials are involved, such as might be encountered in an industrial environment.

While the invention has been illustrated and described in detail in the drawings and foregoing description the same is to be considered as illustrative and not restrictive in character, it being understood that only the preferred embodiment has been shown and described and that all changes and modifications that come within the spirit of the invention are desired to be protected.

What is claimed is:

1. A portable suction device, comprising:

a support frame;

rotation means supported by said support frame for providing rotary motion; and disposable and readily removable collection means supported by said support frame for removing and collecting a suspension when said rotation means is providing rotary motion, said collection means including;

a suction tube;

a collection container;

a pump, having a working member operating on the suspension being pumped and a rigid housing in which the working member operates, wherein said suspension is pumped between said working member and said rigid housing, said pump being connected at its inlet to said suction tube and at its outlet to said collection container, said pump having coupling means for allowing readily operable coupling and decoupling to the output of said rotation means;

wherein said collection means is a unitary assembly suitable for coupling and decoupling in assembled form to the output of said rotation means and in which the pump is essentially entirely non-metallic.

2. The portable suction device for claim 1 in which essentially the entire collection means is plastic.

3. The portable suction device of claim 2 wherein:
said pump is a rotary vane pump and said working member includes a rotor/vane assembly contacting the suspension and operable to pump the suspension through said pump.

4. The portable suction device of claim 3, wherein said rotary vane pump further comprises:
a pump body having a hollow interior portion bounded by a circumferential bearing surface and having approximately diametrically opposed inlet and outlet ports;
said rotor/vane assembly being rotatable within said interior portion and eccentrically mounted whereby the point of greatest spacing of said assembly from said circumferential bearing surface lies in a plane positioned approximately midway between said inlet and outlet ports.

5. The portable suction device of claim 4, wherein:
said rotary vane pump includes a housing with an inner circumferential bearing surface, said housing composed of a plastic; and
the vanes in said rotor/vane assembly are composed of a softer plastic such that said vanes sealingly conform to said bearing surface during operation and the vanes wear more rapidly during operation than said bearing surface.

6. A portable suction device comprising:
rotation means for providing rotary motion; and
disposable and readily removeable collection means for removing and collecting a suspension when said rotation means is providing rotary motion, including;
a suction tube;
a collection container;
a pump, having a working member operating on the suspension being pumped and a rigid housing in which the working member operates, said pump being connected at its inlet to said suction tube and at its outlet to said collection container, said pump having coupling means for allowing readily operable coupling and decoupling to the output of said rotation means; and
a tube retainer mounted near the open end of said suction tube for use when said disposable collection means is decoupled from said rotation means and including;
a receiver barrel having a tapered opening at one end sized to receive the open end of said suction tube in press-fit engagement to seal the end of the tube against liquid leakage; and
a clamp integral with said receiver barrel for holding the suction tube in said press-fit engagement.

7. A portable suction device, comprising:
a support frame;
rotation means supported by said support frame for providing rotary motion; and
disposable and readily removable collection means supported by said support frame for removing and collecting a suspension when said rotation means is providing rotary motion, said collection means including;
a suction tube;
a collection container;
a pump, having a working member operating on the suspension being pumped and a rigid housing in which the working member operates, wherein said suspension is pumped between said working member and said rigid housing, said pump being connected at its inlet to said suction tube and at its outlet to said collection container, said pump having coupling means for allowing readily operable coupling and decoupling to the output of said rotation means;
wherein the collection means is completely liquid sealed (except for the inlet of the suction tube) during operation regardless of orientation.

8. A portable suction device, comprising:
a support frame;
rotation means supported by said support frame for providing rotary motion; and
disposable and readily removable collection means supported by said support frame for removing and collecting a suspension when said rotation means is providing rotary motion, said collection means including;
a suction tube;
a collection container;
a pump, having a working member operating on the suspension being pumped and a rigid housing in which the working member operates, wherein said suspension is pumped between said working member and said rigid housing, said pump being connected at its inlet to said suction tube and at its outlet to said collection container, said pump having coupling means for allowing readily operable coupling and decoupling to the output of said rotation means;
wherein said collection container is a fluid sealed flexible bag with a hydrophobic vent.

9. The portable suction device of claim 1, wherein said support frame includes means for separately readily removably mounting said rotation means and said collection container therein.

10. A portable suction device, comprising:
a support frame;
rotation means supported by said support frame for providing rotary motion; and
disposable and readily removable collection means supported by said support frame for removing and collecting a suspension when said rotation means is providing rotary motion, said collection means including;
a suction tube;
a collection container;
a pump, having a working member operating on the suspension being pumped and a rigid housing in which the working member operates, wherein said suspension is pumped between said working member and said rigid housing, said pump being connected at its inlet to said suction tube and at its outlet to said collection container, said pump having coupling means for allowing readily operable coupling and decoupling to the output of said rotation means;
wherein said support frame includes means for separately readily removably mounting said rotation means and said collection container therein; and
further wherein said collection container comprises a liquid sealed flexible bag gathered within said support frame, having a first usable volume capacity when gathered within said support frame and a larger second usable volume capacity when ungathered to extend outside said support frame.

11. A portable suction device, comprising:

a support frame;

rotation means supported by said support frame for providing rotary motion; and disposable and readily removable collection means supported by said support frame for removing and collecting a suspension when said rotation means is providing rotary motion, said collection means including;

a suction tube;

a collection container;

a pump, having a working member operating on the suspension being pumped and a rigid housing in which the working member operates, wherein said suspension is pumped between said working member and said rigid housing, said pump being connected at its inlet to said suction tube and at its outlet to said collection container, said pump having coupling means for allowing readily operable coupling and decoupling to the output of said rotation means;

wherein said coupling means includes:

said working member having a first interface portion; and an output coupling affixed to the output of said rotation means, said output coupling having a second interface portion;

wherein said first and second interface portions include complementary surfaces such that said pump is operably coupled to the output of said rotation means when the complementary surfaces of said first and second interface portions are in abutting engagement, regardless of the angular orientation of said working member relative to said output coupling prior to said operably coupled abutting engagement, and decoupled otherwise.

12. A portable suction device comprising:

rotation means for providing rotary motion; and disposable and readily removeable collection means for removing and collecting a suspension when said rotation means is providing rotary motion, including;

a suction tube;

a collection container;

a pump, having a working member operating on the suspension being pumped and a rigid housing in which the working member operates, said pump being connected at its inlet to said suction tube and its outlet to said collection container, said pump having coupling means for allowing readily operably coupling and decoupling to the output of said rotation means;

wherein said coupling means includes;

said working member having a first interface portion; and an output coupling affixed to the output of said rotation means, said output coupling having a second interface portion;

wherein said second interface portions include complemeatary surfaces such that said pump is operably coupled to the output of said rotation means when the complementary surfaces of said first and second interface portions are in abutting engagement and decoupled otherwise; and further wherein;

said rotation means includes a housing; and said coupling means further includes;

a male portion on either of said pump or said housing;

a female portion on the other of said pump or said housing for receiving said male portion therein; and said male and female portions being so configured such that when said male portion is received within said female portion, said male and female portions can be moved relative to each other from a first position in which said pump can be removed from said housing to a second position in which said pump cannot be removed from said housing;

wherein, when said male and female portions are in said first position, said first and second interface portions are in abutting engagement.

13. The portable suction device of claim 1 wherein:

said pump is a rotary vane pump and said working member includes a rotor/vane assembly contacting the suspension and operable to pump the suspension through said pump.

14. The portable suction device of claim 13, wherein said rotary vane pump further comprises:

a pump body having a hollow interior portion bounded by a circumferential bearing surface and having approximately diametrically opposed inlet and outlet ports;

said rotor/vane assembly being rotatable within said interior portion and eccentrically mounted whereby the point of greatest spacing of said assembly from said circumferential bearing surface lies in a plane positioned approximately midway between said inlet and outlet ports.

15. The portable suction device of claim 1, wherein:

said pump is operable to produce a plurality of discrete vacuum ranges at said suction tube; and said rotation means includes an electric motor controlled by a solid state electrical control unit for providing a plurality of discrete rotational speed ranges corresponding to said plurality of discrete vacuum ranges.

16. The portable suction device of claim 15 further comprising:

a support frame having means for separately readily removably mounting said motor, said electrical control unit and said collection container therein.

17. A portable suction device, comprising:

rotation means for providing motion; and disposable and readily removeable collection means for removing and collecting a suspension when said rotation means is providing rotary motion, including;

a suction tube;

a collection container;

a pump, having a working member operating on the suspension being pumped and a rigid housing in which the working member operates, said pump being connected at its inlet to said suction tube and at its outlet to said collection container, said pump having coupling means for allowing readily operable coupling and decoupling to the output of said rotation means;

a collection tube connected between the outlet of said pump and said collection container; and means, mounted on said collection tube, for impinging said collection tube so that the tube can be severed and the collection container removed after the suspension is collected without liquid leakage through said tube.

18. The portable suction device of claim 3, wherein said rotary vane pump includes a rotor having spring biased vanes.

19. A portable suction device, comprising:
suction means for removing and collecting a suspension, including;
a suction tube;
a collection container;
a rotary vane pump, connected at its inlet to said suction tube and at its outlet to said collection container operable to pump the suspension through said suction tube and said rotary vane pump into said collection container; and
rotation means for providing rotary motion to said rotary vane pump;
wherein said rotary vane pump includes a rotor/vane assembly and a housing with a lubricated inner circumferential bearing surface, said inner bearing surface being a rapidly wearable, porous plastic which includes lubricant in its pores, said surface being adapted to erode as the vanes travel over it whereby lubricant is continually released from said inner bearing surface during operation of said pump.

20. A modular portable suction device, comprising:
a support frame;
means, removably mounted in said frame, for providing rotary motion;
power supply means, removably mounted in said frame, for energizing said rotary motion means;
suction means for removing and collecting a suspension, including;
a suction tube;
a vacuum pump connected at its inlet to said suction tube and removably mounted to said rotary motion means;
a collection tube connected to the outlet of said vacuum pump; and
a collection container connected to said collection tube comprising a liquid sealed flexible bag gathered within said support frame, having a first usable volume capacity when gathered within said support frame and a larger second usable volume capacity when ungathered to extend outside said support frame.

21. A modular portable suction device, comprising:
a support frame;
means, removably mounted in said frame, for providing rotary motion;
power supply means, removably mounted in said frame, for energizing said rotary motion means;
suction means for removing and collecting a suspension, including;
a suction tube;
a vacuum pump connected at its inlet to said suction tube and removably mounted to said rotary motion means; and
a collection tube connected to the outlet of said vacuum pump; and
a collection container connected to said collection tube; wherein;
said portable suction device is housed within a flexible carrying case having several individual readily openable and closeable openings each providing access respectively to one of the components selected from the group consisting of said rotary motion means, power supply means, suction means, and collection container.

22. The modular portable suction device of claim 21, wherein:
said collection container comprises a liquid sealed flexible bag gathered within said support frame, having a first volume capacity when gathered and a larger second volume capacity when ungathered to extend outside said support frame; and
said carrying case includes a readily openable and closeable opening for said flexible bag to extend through when ungathered.

23. A portable suction device, comprising:
a power supply;
a motor energized by said power supply;
suction means for collecting a suspension, including a vacuum pump operably connected to said motor, a suction tube connected to the inlet of said pump, and an inflatable collection bag for collecting the suspension, without liquid leakage, connected to the output of said pump; and
hydrophobic vent connected to said collection bag, whereby said suction means is operable in any orientation to provide suction at said suction tube and to provide, without liquid leakage, pressure to said collection bag until the suspension collected in said collection bag occludes said hydrophobic vent.

24. A portable suction device, comprising:
a power supply;
a motor energized by said power supply;
suction means for collecting a suspension, including a vacuum pump operably connected to said motor, a suction tube connected to the inlet of said pump, and an inflatable collection bag for collecting the suspension, without liquid leakage, connected to the output of said pump; and
a hydrophobic vent connected to said collection bag, whereby said suction means is operable in any orientation to provide suction at said suction tube and to provide, without liquid leakage, pressure to said collection bag until the suspension collected in said collection bag occludes said hydrophobic vent;
wherein said pump is a rotary vane pump including:
a housing having a pump chamber and a spindle bore;
a rotor/vane assembly rotatable within said chamber having a spindle extending through said spindle bore and operably connected to said motor;
wherein, said spindle bore includes a chamfered recess and said spindle includes a complementary beveled portion situated within said chamfered recess, whereby when a vacuum is created in said pump chamber during operation, said spindle remains liquid sealed in said spindle bore while rotating within the bore.

* * * * *

UNITED STATES PATENT AND TRADEMARK OFFICE
CERTIFICATE OF CORRECTION

PATENT NO. : 4,930,997

DATED : June 5, 1990

INVENTOR(S) : Alan N. Bennett

It is certified that error appears in the above-identified patent and that said Letters Patent is hereby corrected as shown below:

In column 3, line 53, please change "DESCRIpTION OF THE pREFERRED to --DESCRIPTION OF THE PREFERRED--.

In column 11, line 52, please change "curVature" to --curvature--.

In column 11, line 56, please change "4 and" to --43 and--

In column 13, line 41, please change "50 Inlet" to --50. Inlet--.

In column 15, line 58, please change "reserVoir" to --reservoir--.

In column 17, line 60, please change "375-40 Cmm" to --375-400 mm--.

Signed and Sealed this

Thirteenth Day of August, 1991

Attest:

HARRY F. MANBECK, JR.

*Attesting Officer*     *Commissioner of Patents and Trademarks*